United States Patent
Gagnon

(10) Patent No.: US 10,174,076 B2
(45) Date of Patent: *Jan. 8, 2019

(54) PROTEIN PURIFICATION PROCESS

(71) Applicant: AGENCY FOR SCIENCE, TECHNOLOGY AND RESEARCH, Connexis (SG)

(72) Inventor: Peter Stanley Gagnon, Centros (SG)

(73) Assignee: AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 321 days.

This patent is subject to a terminal disclaimer.

(21) Appl. No.: 14/894,993

(22) PCT Filed: Feb. 27, 2014

(86) PCT No.: PCT/SG2014/000090
§ 371 (c)(1),
(2) Date: Nov. 30, 2015

(87) PCT Pub. No.: WO2014/196926
PCT Pub. Date: Dec. 11, 2014

(65) Prior Publication Data
US 2016/0115194 A1   Apr. 28, 2016

Related U.S. Application Data

(60) Provisional application No. 61/831,099, filed on Jun. 4, 2013, provisional application No. 61/859,772, filed on Jul. 29, 2013, provisional application No. 61/907,877, filed on Nov. 22, 2013.

(51) Int. Cl.
| C07K 1/30 | (2006.01) |
| C07K 1/34 | (2006.01) |
| C07K 16/00 | (2006.01) |
| C07K 1/36 | (2006.01) |
| C07K 16/32 | (2006.01) |

(52) U.S. Cl.
CPC .......... *C07K 1/36* (2013.01); *C07K 1/30* (2013.01); *C07K 1/34* (2013.01); *C07K 16/00* (2013.01); *C07K 16/32* (2013.01)

(58) Field of Classification Search
None
See application file for complete search history.

(56) References Cited

U.S. PATENT DOCUMENTS

| 5,283,339 | A * | 2/1994 | Arnold | C07K 1/22 548/104 |
| 7,186,410 | B2 * | 3/2007 | Chtourou | C07K 16/065 424/176.1 |
| 2003/0133829 | A1 * | 7/2003 | Anderle | A61L 2/0088 422/28 |
| 2012/0101262 | A1 | 4/2012 | Arunakumari et al. | |

FOREIGN PATENT DOCUMENTS

| JP | S63-283596 | | 11/1988 | | |
| WO | WO-2005073252 | A1 * | 8/2005 | ............ | A61L 2/0011 |
| WO | WO-2010151632 | A1 * | 12/2010 | ............... | C07K 1/30 |

OTHER PUBLICATIONS

Bresolin et al. "Adsorption of human serum proteins onto TREN-agarose: purificaiton of human IgG by negative chromatography" J. Chromatography B, 877 17-23 (Year: 2009).*
Liu et al. "Recovery and purificaiton process development for monoclonal antibody production" mAbs 2:5, 480-499 (Year: 2010).*
Gan et al. "Characterization and removal of aggregates formed by nonspecific interaction of IgM monoclonal antibodies with chromatin catabolites during cell culture production" J. Chromatography A, 1291 33-40 (Year: 2013).*
Gagnon, "Purification Tools for Monoclonal Antibodies", Validated Biosystems, 1996, pp. 1-269.
European Office Action dated Nov. 11, 2016 for Appln. No. 14807348.9.
Gan et al., "Characterization and removal of aggregates formed by nonspecific interaction of IgM monoclonal antibodies with chromatin catabolites during cell culture production", Journal of Chromatography A 1291, (2013), pp. 33-40.
Chanutin, et al., "The precipitation of Plasma Proteins by Short-Chain Fatty Acids"; Arch. Biochem. Biophys. 89 (1960) pp. 218-220.
Brodsky et al, "Caprylic acid precipitation method for impurity reduction: an alternative to conventional chromatography for monoclonal antibody purification", Biotechnol. Bioeng. 109 (2012), pp. 2589-2598.
Vagenende et al., "Amide-mediated hydrogen bonding at organic crystal/water interfaces enables selective endotoxin binding with picomolar affinity", AACS. Appl. Mater. Interfaces, 22 (2013) pp. 4472-4478.
Morais et al, "A model mechanism for protein precipitation by caprylic acid: Application to plasma purification", vol. 59, No. 1, 2012, pp. 50-54.

(Continued)

*Primary Examiner* — Daniel E Kolker
*Assistant Examiner* — James L Rogers
(74) *Attorney, Agent, or Firm* — Pillsbury Winthrop Shaw Pittman, LLP

(57) ABSTRACT

A method of purifying a target protein includes contacting a cell culture harvest or a protein preparation including at least one target protein with at least one fatty acid having 8 to 10 carbon atoms to form a mixture, contacting the mixture with one or more solids to form a mixture, the one or more solids comprise a cationic functional group, a metal binding functional group, or both, the metal binding functional group including a nitrogen-containing moiety selected from (1) a polyamine, (2) an imine, (3) an N-heterocycle, (4) an amino acid, (5) an N-hydroxyamide, (6), an arylamine, and combinations thereof, and separating solid materials after contacting the mixture with the one or more solids to provide a solution comprising the target protein.

13 Claims, No Drawings

(56) References Cited

OTHER PUBLICATIONS

Vagenende et al, "Allantoin as a solid phase adsorbent for removing endotoxins" Journal of Chromatography A, 1310 (2013), pp. 15-20.
Kuczewski et al., "A single-use purification process for the production of a monoclonal antibody produced in a PER.C6 human cell line", Biotechnology Journal, 2011, 6, pp. 56-65.
Lain et al., "PEG precipitation: a powerful tool for monoclonal antibody purification", BioPharm, 2010, pp. 1-8.
McKinney et al., "A simple non-chromatographic procedure to purify immunoglobulins from serum and ascites fluid", Journal of Immunological Methods, 96, (1987), pp. 271-278.
English translation of Japanese Office Action dated Dec. 12, 2017, for related Japanese patent application No. 2016-518306.
Horio, Takeichi, Table 2·2 Structure and Properties of Surfactants, Fundamental Experimental Methods for Proteins and Enzymes, 2000, Revision 2nd edition, pp. 66-67.
Written Opinion dated Aug. 4, 2017, in Singapore Patent Application No. 11201505204V.
Temponi, M., et al., "Purification of murine IgG monoclonal antibodies by precipitation with caprylic acid: comparison with other methods of purification," Hybridoma, 1989, vol. 8, No. 1, pp. 85-95.
Gagnon, P., "Technology trends in antibody purification," Journal of Chromatography A. 2012, vol. 1221, pp. 57-70.

\* cited by examiner

PROTEIN PURIFICATION PROCESS

Embodiments disclosed herein relate to methods for purifying proteins, including antibodies, such as IgG and IgM antibodies.

BACKGROUND

Purification of proteins typically begins with a clarification step in which cells and debris are removed so that the remaining supernatant can be processed by methods that would otherwise be hampered by their presence. Their removal commonly involves physical methods such as centrifugation and filtration. This step sometimes involves the use of filtration materials with anion exchange capabilities, or the addition of anion exchange particles or soluble polymers directly to the antibody-containing harvest (Gagnon, P., Purification Tools for Monoclonal Antibodies, Validated Biosystems, Tucson, 1996; Kuczewski, M., et al, *Biopharm Int.* 23(3) (2010) 20-25; Kuczewski, M., et al, *Biotechnol. J.*, 6 (2011) 56-65.

Secondary treatment of physically clarified cell culture harvests with allantoin, soluble organic cations, and mixed particles has been described (Gan, H. et al J. Chromatogr. A, 1291 (2013) 33-40). This approach particularly reduced the content of chromatin expelled by dead cells and the levels of aggregates associated with chromatin, but three chromatography steps were subsequently needed to achieve the desired purity. Allantoin is an FDA-approved anti-inflammatory agent used widely in over-the-counter healthcare products. It is known to remove endotoxin from protein solutions, including from solutions of IgG, apparently through hydrogen bonding (Vagenende et al, ACS. Appl. Mater. Interfaces, 22 (2013) 4472-4478; Vagenende et al, J. Chromatogr. A 1310 (2013) 15-20).

Partial purification of IgG antibodies by contaminant co-precipitation with caprylic acid (octanoic acid) has been disclosed (Chantuin, A., et al, Arch. Biochem. Biophys. 89 (1960) 218-220; McKinney, M. et al, J. Immunol. Met., 96 (1987) 271-278). The fatty acid binds to all proteins but tends particularly to precipitate acidic non-IgG contaminants (Gagnon supra; Morais, V., et al, Biotechnol. Appl. Biochem., 59 (2012) 50-54). The mechanism and process development guidelines for application to cell culture harvests have been indicated (Gagnon supra), including basic variables such caprylic acid concentration, pH, salt concentration, temperature, and the need for a subsequent chromatography step to remove residual caprylic acid from the soluble IgG preparation. The technique is most often described to prepare crude samples for subsequent purification by other means (Gagnon supra; Y. Yigsaw et al, 2008, Improving upstream feed stock to downstream operations, Recovery of Biologics Conference XIII, Quebec; Arunakumari, A. et al, US Patent Application 20120101262 A1), but has also been applied as a polishing step following antibody capture by protein A affinity chromatography (Y. Brodsky et al Biotechnol. Bioeng. 109 (2012) 2589-2598).

SUMMARY

In some aspects, embodiments disclosed herein relate to methods of purifying a target protein comprising contacting a cell culture harvest with at least one fatty acid having 7 to 10 carbon atoms to form a mixture, contacting the mixture with one or more solid or soluble materials to form a mixture, wherein the one or more solid or soluble materials comprise a cationic functional group and a metal binding functional group, the metal binding functional group comprising a nitrogen-containing moiety selected from the group consisting of (1) a polyamine, (2) an imine, (3) an N-heterocycle, (4) an amino acid, (5) an N-hydroxyamide, (6), an arylamine, and combinations thereof, and separating solid materials after contacting the mixture with the one or more electrostatically charged solids to provide a solution comprising the target protein. The processed liquid may optionally, be further passed through a device with an internal contact surface contact that comprises positive charges before being processed by other purification methods, if desired.

In some aspects, embodiments disclosed herein relate to methods for purifying a target protein comprising contacting a cell culture harvest with at least one fatty acid having 7 to 10 carbon atoms to form a mixture, contacting the mixture with allantoin, and separating solid materials after contacting the mixture with allantoin to provide a solution comprising the target protein.

In some aspects, embodiments disclosed herein relate to methods of purifying an antibody comprising contacting a cell culture harvest with at least one fatty acid having 7 to 10 carbon atoms to form a mixture, contacting the mixture with one or more solid or soluble materials to form a mixture, wherein the one or more solid or soluble materials comprise a cationic functional group and a metal binding functional group, the metal binding functional group comprising a nitrogen-containing moiety selected from the group consisting of (1) a polyamine, (2) an imine, (3) an N-heterocycle, (4) an amino acid, (5) an N-hydroxyamide, (6), an arylamine, and combinations thereof, and separating solid materials after contacting the mixture with the one or more electrostatically charged solids to provide a solution comprising the antibody. The processed liquid may optionally, in addition, be passed through a device with an internal contact surface contact that embodies positive charges before being processed by other purification methods, if desired.

In some aspects, embodiments disclosed herein relate to methods for purifying an antibody comprising contacting a cell culture harvest with at least one fatty acid having 7 to 10 carbon atoms to form a mixture, contacting the mixture with allantoin, and separating solid materials after contacting the mixture with allantoin to provide a solution comprising the antibody.

DETAILED DESCRIPTION

It has been discovered that a combination of materials that are chemically antagonistic to one another has the unexpected effect of providing target proteins, including antibodies, at a higher level of purity and a lower level of turbidity than purification methods relying on any one of the materials individually. Combinations of antagonistic materials would normally be expected to cancel each others' individual effects and result in inferior protein purification, inferior protein recovery, or both. Instead, the present embodiments provide defined windows within which the materials work synergistically to achieve levels of protein purity and recovery that are substantially beyond the ability of any of the individual components to provide. These observations are particularly applicable to antibodies, such as IgG and IgM antibodies. In addition, experimental results indicate that reactivity curves for each of the components in the combination is distinct from their reactivity curves when used individually. This highlights that the utility of the embodiments disclosed herein could not have been predicted by the known properties or applications of the individual components. The components to be combined may include saturated fatty acids containing 7 or 8 or 9 or 10 carbon atoms, or unsaturated fatty acids containing 6 or 7 or 8 or 9 carbon atoms with one double bond, and soluble and/or solid materials bearing a positive charge. They may, further include one or more solid or soluble materials that comprise a metal binding functional group. They may further include allantoin. In the methods disclosed herein, the materials are combined in a liquid preparation containing a target protein, such as a species of antibody, then after a suitable period of incubation, solids are removed to provide a solution comprising the antibody, absent up to 99% or more of host cell contaminants, with an average recovery, in the case of IgG antibodies, of about 90 to about 95%, and a turbidity of less than about 5 NTU (nephelometric turbidity units).

Experimental data document the mutually antagonistic interactions among the components employed in methods disclosed herein. For example, a cationic (electropositive) component and an anionic (electronegative) component such as a fatty acid, are understood to have an attraction to one another, and their interaction should tend to reduce the ability of either one to interact with other components of an antibody preparation such as in a cell culture harvest. This is indicated by data showing that certain contaminants, such as antibody light chains, are removed by a combination of components at one ratio, but re-appear in the antibody-containing liquid if the proportion of the cationic component is increased. In one particular example, this is believed to occur because a fatty acid bound to a contaminant within a precipitate is more strongly attracted to a cationic solid than it is to the contaminant, so that when the amount of the cationic solid is increased, the fatty acid transfers to that solid, which liberates the contaminant from the precipitate, causing it to re-contaminate the antibody preparation. In another example of mutual antagonism, crystalline allantoin has been shown experimentally to bind more than 99% of the fatty acids in cell culture harvest, indicating a high likelihood that it acts on added fatty acids in a similar manner. This should be expected to reduce the effectiveness of fatty acids added to an antibody-containing cell culture harvest for the purpose of precipitating non-antibody contaminants. To the contrary, this aspect of the invention contributes to effective use of fatty acids at concentrations less than half the levels reported as optimum in the scientific literature. Without being bound by theory, it may be that fatty acids complexed to undissolved allantoin through hydrogen bonding conserve their native charge, hydrophobicity, and ability to bind contaminants, while the physical density of the undissolved allantoin enhances their removal by sedimentation. In another example of mutual antagonism, addition of anionic chelating solids—which should be inert to fatty acids—to a mixture of fatty acids and cationic chelating solids, releases contaminants back to the antibody solution that were successfully removed by the already-antagonistic combination of cationic solids and fatty acids.

In another example of mutual antagonism, the addition of very low concentrations of nonionic surfactants that weaken hydrophobic interactions, and would thereby be expected to interfere with the ability of fatty acids to achieve their effects, surprisingly improves the effectiveness of removing free light chain contaminants, while larger amounts compromise removal of acidic non-antibody proteins. In another, surprising example, low levels of cationic surfactants, which should interfere with both the charge and hydrophobic effects of fatty acids, roughly double the ability of the combination to remove acidic non-antibody proteins, and double or triple aggregate removal, while higher concentrations have the opposite effect. These examples highlight that when normally antagonistic components are combined in properly balanced proportions, they can create windows within which it is possible to remove contaminants that are not removed in the absence of antagonists. The enhancement provided by antagonists is substantial in many cases that overall purification performance of the disclosed methods exceeds the capabilities of protein A affinity chromatography, which is generally regarded as the highest performing antibody purification method available.

It has also been discovered that the inclusion of functionalized solid materials with the ability to bind metal ions contributes to higher purity, and lower aggregate content of processed antibody. Soluble chelating agents surprisingly failed to produce this benefit. Without being bound by any theory, this effect may be mediated by preferential transfer of metal ions from the surface of an antibody to the solid-bound metal affinity ligand, with the effect of reducing hydrophobic and electrostatic heterogeneity of the antibody induced by interaction with metal ions; or by having the same effect on contaminating proteins and thereby altering their chemical behavior to make them more responsive to the disclosed methods. It may alternatively reflect the influence of a secondary feature of metal binding ligands not mediated through metals.

It has been further discovered that the inclusion of allantoin particularly enhances the ability of fatty acid precipitation to remove particulates. Without being bound by theory, the effects of allantoin are believed to be mediated through hydrogen bonding, by which large molecular assemblages, including ultra-small particles, including viruses, are bound to the larger allantoin crystals. Due to its relatively high density of 1.45 g per cubic cm, allantoin crystals promote rapid gravimetric sedimentation of associated materials, and enhance their sedimentation by centrifugation. Allantoin crystals also alter the physical constitution of fatty acid-contaminant precipitates from a typically gluey sludge, to a more cake-like consistency that facilitates the passage of liquid and improves filtration efficiency. A portion of the allantoin added to an aqueous solution dissolves, up to a maximum of about 36 mM, and is believed to weaken hydrophobic interactions of proteins with fatty acids. Dissolved allantoin is understood to remain in the antibody-containing solution after removal of solids. While these features are welcome, they represent a paradox since experimental data indicate that allantoin binds 99.7% of fatty acids from cell culture harvests. As this implies, the proportion of allantoin must be carefully controlled. The appropriate proportion for a give application is determined by simple experimentation, generally starting with 1-2% (w/v).

It has also been discovered that methods disclosed herein unexpectedly allow saturated fatty acids with 7 or 9 or 10 carbon atoms to be substituted for caprylic acid. Enanthic (heptanoic) acid contains 7 carbons. Pelargonic (nonanoic) acid contains 9 carbons. Capric (decanoic) acid contains 10 carbons. Even more surprisingly, unsaturated fatty acids with 6 or 7 or 8 or 9 carbon atoms and 1 double bond are effective. Despite species other than octanoic acid being neglected in the art for antibody purification, experimental data indicate that more hydrophobic fatty acids more effectively remove antibody aggregates and fragments than caprylic acid, though at higher risk of reducing antibody recovery.

Experimental data indicate that methods disclosed herein may A) achieve 0.10-fold more effective removal of particulates than caprylic acid treatment alone, achieving a turbidity of about 2 nephelometric turbidity units (NTU), versus 20 NTU or higher achieved with just caprylic acid alone (Brodsky et al supra); B) increase IgG purity to greater than 99%, usually greater than 99.9%; C) reduce aggregate content to 1% or less, typically to less than 0.5%, and frequently to less than 0.05%; D) reduce content of antibody-related fragments to 1% or less; E) enhance removal of DNA, endotoxin, and virus; F) support 90-95% recovery of IgG; and F) permit such purification to be achieved even within the bioreactor within which the cells are grown, thereby increasing process efficiency. It will be noted individual results for some of these measures may be achieved in certain instances by traditional contaminant co-precipitation with fatty acids, but not all of them in a single operation, as achieved by the methods disclosed herein.

Experimental data further demonstrate the surprising discovery that methods disclosed herein particularly remove contaminants that interfere with traditional fractionation methods that might be used to otherwise or additionally purify antibodies. The methods may allow low-functioning fractionation methods, such as ultrafiltration, or precipitation by salts, or precipitation by nonionic organic polymers, to achieve levels of purification otherwise achievable only with high-functioning fractionation methods such as protein A affinity chromatography. For example, initial purification with the disclosed methods, followed by ultrafiltration or ammonium sulfate precipitation, followed by anion exchange chromatography, reduces host proteins to less than 1 ppm and aggregates to less than 0.05%. Equally surprising, the methods disclosed herein may impart high-functioning fractionation methods with the ability to achieve purity hundreds of times greater than they are typically able to achieve. For example, where protein A affinity chromatography typically reduces host protein contamination to the range of about 500 to 2000 parts per million (ppm), protein A chromatography practiced following the disclosed methods reduces host protein contamination to less than 1 ppm.

In one exemplary embodiment that illustrates the integration of numerous aspects of the methods disclosed herein, allantoin is added to an antibody-containing cell culture harvest in an amount to produce a final concentration of 1% (w/v), followed by addition of capric acid in an amount to produce a final concentration of 0.2% (v:v). The mixture is incubated for 2 hours, during which a precipitate is formed by the interaction of capric acid with contaminants, and which is interspersed with undissolved allantoin crystals. This step is followed by addition of polymeric particles functionalized with TREN in an amount to produce a final concentration of 5% (v:v), and incubated for a period of 4 hours. TREN (tris(2-aminoethyl)amine) is an electropositive metal binding compound that may be immobilized on polymer particles or other functionalized solids. Such materials are marketed for the purpose of conducting immobilized metal affinity chromatography. Mixing is terminated and the solids, consisting of capric acid-contaminant precipitates, residual capric acid, undissolved allantoin, and the TREN particles, are removed by any expedient method. In a related embodiment, the TREN particles are replaced by particles functionalized with an alternative positively charged metal-binding species. In a related embodiment, the positively charged metal-binding particles are replaced by a combination of particles, some functionalized with a positively charged amine-based ion exchanger, and some functionalized with a negatively charged metal binding species. In a related embodiment, only positively charged particles lacking metal affinity may be present. In related embodiments, particles functionalized with other chemical species may be present. In a related embodiment, the substantially solids-free antibody-containing liquid is further processed by passage through an electropositive depth filter, or other device in which the sample contacts an electropositive or other functionalized surface, and which may provide the additional benefit of scavenging residual fatty acid or other soluble non-antibody species from the sample.

In another exemplary embodiment that illustrates integration of various aspects of the methods disclosed herein, allantoin is added to cell culture harvest in an amount to produce a final concentration of 2% (w/v) followed by addition of capric acid in an amount to produce a final concentration of 0.2% (v:v). The mixture is incubated for 2 hours, during which a precipitate is formed by the interaction of capric acid with contaminants, and which is interspersed with undissolved allantoin crystals. The mixture is then contacted with a device comprising at least one functionalized solid that retains capric acid-contaminant precipitates interspersed with undissolved allantoin but permits the passage of liquid.

In another exemplary embodiment that illustrates integration of various aspects of the methods disclosed herein, allantoin is added to cell culture harvest in an amount to produce a final concentration of 1% (w/v) followed by addition of capric acid in an amount to produce a final concentration of 0.2% (v:v). The mixture is incubated for 2 hours, during which time a precipitate is formed by the interaction of capric acid with contaminants, and which is interspersed with undissolved allantoin crystals. Capric acid-contaminant precipitates interspersed with undissolved allantoin are removed by any expedient method and the liquid is contacted with a device comprising at least one functionalized surface.

In another exemplary embodiment that illustrates integration of various aspects of the methods disclosed herein, allantoin is added to cell culture harvest in an amount to produce a final concentration of 1% (w/v) followed by addition of capric acid in an amount to produce a final concentration of 0.2% (v:v). The mixture is incubated for 2 hours, during which time a precipitate is formed by the interaction of capric acid with contaminants, and which is interspersed with undissolved allantoin crystals. This step is followed by addition of functionalized polymeric particles and incubated for 4 hours. The solids are removed using a device comprising at least one functionalized surface. In some embodiments, the processed liquid is passed through a depth filter including a positively charged contact surface before further processing.

In some embodiments, about 0.2% capric acid may be replaced with pelargonic acid at a concentration of about 0.3%, or caprylic acid at a concentration of about 0.4% or enanthic acid at a concentration of about 0.6%. This reveals the dependency of contaminant removal and antibody recovery on the concentration and hydrophobicity of the fatty acid. Experimental data reveal that the more hydrophobic the fatty acid, the lower the concentration needed to achieve a good result, and also the lower the concentration to compromise IgG antibody recovery. It will be understood that the absolute and relative concentration may vary from one antibody to another and that the above concentrations of the specific fatty acids may therefore vary, but such values are provided to provide guidance to the skilled artisan for a convenient starting point when assessing purification a previously uncharacterized antibody.

In some embodiments, about 0.2% caprylic acid may support more effective aggregate removal than at higher concentrations. However, at about 0.4%, more effective removal of free antibody light chain, light-chain dimers, and other fragmentary forms, as well as other contaminants may be achieved. Thus, one skilled in the art will recognize the value of optimizing the concentration of a given fatty acid by consideration of its effects in the context of potential follow-on fractionation methods. If methods disclosed herein are to be followed by a method that is particularly suitable for removal of aggregates, it may be beneficial to optimize the fatty acid concentration to remove antibody fragments. If methods disclosed herein are to be followed by a method particularly suitable for removing fragments, it may be beneficial to optimize the fatty acid concentration to remove aggregates.

In some embodiments, allantoin may be added after the fatty acid. In another related embodiment, allantoin is not added until after the precipitate has formed. In another embodiment allantoin is not added until after the precipitate has been removed. In one specific example of such an embodiment, allantoin and functionalized solids may be added after the precipitate has been removed, and are subsequently removed together in a second solids-removal step. In some embodiments, allantoin is omitted.

In some embodiments, a non-ionic surfactant or a zwitterionic surfactant may be added to the mixture at a concentration below its critical micelle concentration. Experimental data indicate that this improves removal of antibody fragments, while surfactant concentrations above the critical micelle concentration suppress the removal of antibody fragments, though with the offsetting benefit of increasing antibody recovery. In some embodiments, a substantially higher concentration of a non-ionic or zwitterionic surfactant may substantially compromise reduction of acidic host cell proteins.

In some embodiments, a low concentration of a cationic surfactant may substantially enhance the removal of host proteins and DNA. In some such embodiments, the cationic surfactant is hexadecyltrimethylammonium bromide, also known as cetyltrimethylammonium bromide (CTAB); or dodecyltrimethylammonium bromide; or decyltrimethylammonium bromide; or myristyltrimethylammonium bromide; or trimethyloctadecylammonium bromide, or variations with a different positively charged moiety, such as a primary, secondary, or tertiary amino group, or variations with more or fewer carbon atoms. In some such embodiments, 0.01% CTAB may double the amount of host protein removed, whereas 0.05% CTAB may reduce removal efficiency by a factor of 5.

In some embodiments, adding a low concentration of a cationic surfactant to a cell culture harvest in advance of a fatty acid may substantially enhance aggregate removal, in some cases by a factor of 2 or 3 over the amount of aggregate removed when the sequence is reversed. In some such embodiments, the cationic surfactant is cetyltrimethylammonium bromide, at a concentration of about 0.01%. In some embodiments, the cationic surfactant may be substituted with other cationic organic compounds, such as ethacridine, methylene blue, chlorhexidine, and benzalkonium chloride. In some such embodiments, it is understood that the optimal amount of the electropositive organic compound will need to be determined individually for each antibody, also taking into account the identity and concentration of the fatty acid.

In some embodiments, the chemically functionalized solids may include at least one nitrogen-containing compound. In some such embodiments, at least one nitrogen-containing compound may embody the ability to bind metal ions. In some such embodiments, at least one nitrogen-containing compound may be negatively charged and may include one or more compounds from the group comprising iminodiacetic acid, nitriloacetic, glutamic acid, aspartic acid, and aminophenyl phosphate, among others. In other such embodiments, at least one nitrogen-containing compound may be positively charged and may include one or more compounds from the group comprising TREN, diethylenetriamine, triethylenetetramine, tetraethylenepentamine, polypropylenimine tetramine, PAMAM dendrimer (ethylenediamine core), deferoxamine (desferioxamine), arginine, histidine, histamine, and imidazole, among others. In other such embodiments, at least one nitrogen-containing compound may include an aliphatic hydrocarbon, and aromatic hydrocarbon, a carbonyl group, a carboxyl group, a sulfo group, a phospho group, or a hydroxyl group.

In some embodiments, one or more chemically functionalized solids may be replaced by or combined with soluble entities chemically functionalized with the same or similar moieties.

In some embodiments, the chemically functionalized solids or soluble entities may include more than one type of substrate solid or soluble entity where each embodies a different nitrogen-containing compound.

In some embodiments, at least one chemically functionalized solid or soluble entity with a nitrogen-containing compound may be combined with another chemically functionalized solid or soluble entity lacking a nitrogen atom, where the nitrogen-lacking compound may include one or more functionalities from the group comprising an aliphatic hydrocarbon, an aromatic hydrocarbon, a carbonyl group, a carboxyl group, a sulfo group, a phospho group, or a hydroxyl group.

In some embodiments, solids may be separated from the antibody-containing solution by any expedient means, including filtration or sedimentation, including one or more treatments from the groups comprising microfiltration, depth filtration, and centrifugation, where depth filtration may be performed with filtration media that are substantially inert or with filtration media that have been chemically functionalized, or combined with materials that are chemically functionalized.

In some embodiments, the one or more species of insoluble materials may be configured in at least one device that supports the passage of liquid but does not allow the passage of solids.

In some embodiments, allantoin may be added at a weight to volume concentration of about 0.6 to about 30%, or about 1 to about 30%, or about 1 to about 10%, or about 1 to about 2%. In some embodiments, allantoin may be omitted. In some embodiments, allantoin may be present in a non-zero amount up to about 0.6%. While the presence of allantoin may be desired at a concentration sufficient that a portion of the added allantoin does not dissolve, such as 1%, methods may produce adequate results in the absence of allantoin, or in the presence of allantoin at a concentration where substantially all of the allantoin is soluble. Experimental data indicate that larger proportions of allantoin, such as 2%, 3%, 4%, 5%, 10% or higher support more effective reduction of aggregates, but also reduce antibody recovery, modestly but measurably. Experimental data also reveal that allantoin can independently reduce levels of virus and endotoxin, by 3 logs or more, and generally produce supernatants that are remarkably clear (2.0 NTU), all of which document that allantoin makes a favorable contribution to methods disclosed herein, when employed. Without being bound to any particular theory, it appears that allantoin's mechanism of action with large biological species and assemblages primarily involves hydrogen bonding, which may, explain in part why its effectiveness is little affected by substantial variations in pH or conductivity. This could also explain why fatty acids bound to allantoin retain their interactivity with contaminants.

In some embodiments, the fatty acid may include one or more species with a general structural formula of $CH_3(CH_2)_nCOOH$, where n is an integer from 4 to 12, inclusive. In some embodiments, n is an integer from 5 to 8. In some such embodiments, the fatty acid may be enanthic acid (heptanoic acid). In some such embodiments, the fatty acid may be caprylic acid (octanoic acid). In some such embodiments, the fatty acid may be pelargonic (nonanoic acid). In some such embodiments, the fatty acid may be capric acid (decanoic acid). In some embodiments, more than one species of fatty acid may be employed. In some embodiments, the fatty acid may be added in the form of a salt, such as a sodium salt, for example sodium caprylate.

In some embodiments, the fatty portion of the fatty acid may consist of a linear "straight" chain of carbon atoms. In some embodiments, the fatty portion of the fatty acid may consist of a branched chain, such as 2-ethylhexanoic acid, which contains a 2-carbon chain at the number 2 position of the primary 6-carbon chain, producing a total of 8 carbon atoms. In some embodiments the fatty acid may be present at a concentration 0.05 to 5%, or 0.1 to 2%, or 0.2 to 0.5%, or an intermediate value.

In some embodiments, the fatty acid may include a double bond. In some such embodiments the double bond may be at any position in the carbon chain. In some such embodiments, the fatty acid chain may contain 6 or 7 or 8 or 9 carbon atoms. In one such embodiment, the fatty acid is nonenoic acid with a terminal double bond. In some embodiments, the fatty acid may be added in the form of a salt. In some embodiments the fatty acid may be present at a concentration 0.05 to 5%, or 0.1 to 2%, or 0.2 to 0.5%, or an intermediate value. In some such embodiments, 0.4% to 0.6% 8-nonenoic acid provides better results than 0.4% caprylic acid.

In some embodiments, employing more than one species of fatty acid, the species may be selected to encompass a range of hydrophobicities, for example the combination of heptanoic and decanoic, acid, or the combination of caprylic and nonanoic acid, or other combinations, potentially including fatty acids of greater or lesser hydrophobicity. In some such embodiments, the proportions of the respective fatty acids may be 10:1, 5:1, 2:1, 1:1, 1:2, 1:5, 1:10, or any intermediate range in between, or other ratios outside of these. In some such combinations the total amount of fatty acid species added to a working solution may be in the range of a non-zero amount up to 0.01%, 0.01 to 0.1%, 0.1 to 1%, 1 to 5%, 0.2 to 0.4%, or an intermediate range or value.

In some embodiments employing more than one species of fatty acid, the total number of species may include 3, or 4, or more, in any proportion; and in any total amount shown by experimental results to provide utility.

In some embodiments, the fatty acid is left to incubate in the antibody preparation for 5 to 360 minutes, or 15 to 240 minutes, or 60 to 120 minutes, or 30 to 60 minutes, or for an intermediate interval, before exposing the mixture to the one or more functionalized solids.

In some embodiments, the temperature at which the fatty acid is incubated may be influenced by the largest species of fatty acid present, since carbon chain length directly influences fatty acid solubility, where the shorter the chain length, the higher the solubility, and where the longer the chain length, the greater the diminution of solubility with decreasing temperature. Thus in all cases, an initial temperature of about 37° C. will solvate a higher concentration of fatty acid than lower temperatures. This favors direct addition of the fatty acid to the harvest immediately following termination of the cell culture. Incubation may subsequently continue at 37° C., still in the bioreactor. It will be apparent that the more hydrophobic the fatty acid, the more sensitive its solubility to temperature, and therefore the more sensitive its functionality to temperature. In some embodiments, higher temperatures may allow the use of fatty acids up to $C_{11}$, $C_{12}$, $C_{13}$, $C_{14}$, $C_{15}$, or even higher. In some embodiments employing lower temperatures, for example where processing is conducted at about 2 to about 8° C., the use of shorter chain fatty acids may be favored, such as $C_8$, $C_7$, $C_6$, or even lower.

In one exemplary embodiment using a solid or soluble substrate functionalized with TREN, TREN is covalently attached to a substrate by one terminal group, creating a species with 2 primary amine nitrogen atoms, 1 secondary amine nitrogen atom, 1 tertiary amine nitrogen, 5 terminal hydrogen atoms, and 3 hydrophobic ethyl groups. In another such embodiment, TREN is covalently attached to a substrate by two terminal groups creating a species with 1 primary amine nitrogen atom, 2 secondary amine nitrogen atoms, 1 tertiary amine nitrogen atom, 4 terminal hydrogen atoms, and 3 ethyl groups. In another such embodiment, TREN is covalently attached to a substrate by three terminal groups, creating a species with 3 secondary amine nitrogen atoms, 1 tertiary amine nitrogen atom, 3 terminal hydrogen atoms, and 3 ethyl groups. In one embodiment, covalently immobilized TREN may be present in any combination or subset of these or other forms.

In one embodiment, a strong metal affinity functionality on an electropositive moiety may be absent. In one such embodiment, a strong metal affinity functionality may be associated with an electronegative chemically reactive group. In one such embodiment, the electronegative groups may also include functional subparts that confer the ability to participate in hydrogen bonding and/or hydrophobic interactions. In one such embodiment, the electronegative group may be iminodiacetic acid, or nitriloacetic acid, or aspartic acid, or glutamic acid, or a combination of negatively charged metal affinity ligands. In one such embodiment, one or more species of negatively charged metal affinity ligand may be resident on one subpopulation of one or more solids, while a multivalent electropositive ligand substantially lacking metal affinity may be resident on another subpopulation of one or more solids.

In one embodiment, one or more solid or soluble substrates functionalized to mediate strong metal affinity functionality via a zwitterionic or nonionic species may be present. Such substrates may be present with one or more solids that bear electropositive metal-binding species, or with one or more substrates that bear electronegative metal-binding species, or electropositive multivalent ligands that lack a strong metal-binding functionality, or electronegative multivalent ligands that lack a strong metal-binding functionality, or non-ionic or zwitterionic ligands that lack a strong metal-binding functionality, or any combination of the above.

It will be apparent that the presence of metal-binding functionality on one or more substrates may be beneficial in methods disclosed herein. Experimental data indicate that such a functionality produces better results than substrates lacking a metal affinity functionality. Without being bound by theory, this effect may be mediated through a decrease in protein charge and/or hydrophobic heterogeneity achieved through removal of metal ions nonspecifically bound to protein surfaces, or dissociation of metal-bridge-complexes where an antibody is bound to a protein, polynucleotide, or other contaminating biological species via a metal ion which is also bound to the other species, or removal of metal ions from metal-phospholipid or metal-phospholipid-fatty acid complexes, or an unknown aspect of the reactivity of fatty acids with proteins, or any combination of the above. Experimental data also indicate, however, that useful results may be obtained in the absence of one or more substrates that bear a metal affinity functionality.

In one embodiment where one or more substrates are provided, the mixture may be incubated for 5 to 960 minutes, or 15 to 720 minutes, or 30 to 480 minutes, or 60 to 240 minutes, or 90 to 120 minutes, or an intermediate interval. In one such embodiment, incubation may occur at about 37° C., or about 22 to about 26° C., or about 2 to about 8° C., or may begin at about 37° C. as a result of just being added to a freshly terminated cell culture harvest then be transferred to about 2 to about 8° C. for incubation over a period of hours. Incubation temperature will be partly determined by the species of fatty acid employed, or if more than one species of fatty acid, by the largest species, since their degree of solubility is a function of the alkyl chain length. For example, the 10-carbon capric acid is soluble at 37° C. but not at about 2 to about 8 degrees. It could be incubated with the harvest initially for a period of time, and then placed at about 2 to about 8 degrees immediately following addition of the insoluble charged multivalent chemically reactive substrates, where the low temperature insolubility of the capric acid might enhance the removal of contaminants.

In one embodiment where one or more solid or soluble substrates are provided, the proportion of substrates to be added to a given volume of fatty acid-treated harvest may be determined by simple experimentation. Current experimental data indicate that TREN covalently immobilized on polymer microspheres at a volumetric proportion of about 2% is adequate to achieve excellent results. In some cases 1% or less may be adequate. In some cases, a proportion greater than 2%, 3%, 4%, or 5% may support better results. As noted however, the higher the availability of TREN, the greater degree of interference with fatty acid precipitation. Experimental data show that excess TREN, for example 10% in some cases, causes contaminants previously removed by fatty acid precipitation to reappear in the antibody-containing solution. It will be understood by the person of skill in the art that the most effective amount of functionalized solid may be determined by simple experimentation. It will be understood equally that the larger the amount of added substrates, the greater the material expense, which will create an opportunity to choose the solution that offers the most desired balance of performance and cost.

In one embodiment where one or more solids are configured in a device that permits the passage of fluids but does not permit the passage of solids, the contact time of the fatty acid-containing sample as it passes through the device may amount to minutes or seconds, depending on the size, efficiency, and construction of the device.

In one embodiment, methods disclosed herein may need no pH adjustment. Addition of the fatty acid may reduce the pH of the harvest to a sufficiently low level, and subsequent scavenging of excess fatty acid by the one or more solids may substantially restore the pH to the original value. In one embodiment, the harvest may be titrated to a particular pH value before addition of the fatty acid, which may add robustness to the method, but which may necessitate that the pH be adjusted again after the method has been performed, potentially for the purpose of preparing the sample to be fractionated to a higher degree of purity by a subsequent method. In one embodiment, the initial pH may be adjusted to a value in the range of 4 to 6, or 4.5 to 5.5, or 4.75 to 5.25, or 5.1 to 5.3, or an intermediate value such as 5.2, or another intermediate value. It will be understood by the person of skill in the art that the optimum pH may vary from one species of antibody to another, and according to the composition of medium in which the antibody is resident. It will be equally understood that the pH employed to achieve optimal results may be more moderate than required with fatty acid precipitation alone due to the contributions of the additional elements of the methods disclosed herein. This is a noteworthy consideration because exposure to the low pH values associated with traditional use of fatty acid precipitation are in a range that may have lasting adverse effects on the antibody. This highlights another unexpected benefit of the disclosed methods.

In one embodiment, methods disclosed herein need not adjust conductivity through either a reduction or increase of salt concentration, such as with water or with NaCl or other salt. Salt concentration is known however to affect antibody recovery and purity, and variations may be explored without departing from the essential features of the method. Experimental evidence indicates that antibody solubility becomes compromised in conditions of low conductivity and low pH, independently from the presence of fatty acids or other additives. Poor antibody solubility translates to an elevated probability of significant antibody loss in conjunction with fatty acid precipitations. This means that reduction of pH may limit the degree to which conductivity can be reduced, and may suggest that conductivity be increased to avoid excessive loss of antibody. Remarkably, the effectiveness of the methods disclosed herein are not substantially decreased by increased conductivity up to 20 mS/cm. This is remarkable because charge interactions are believed to control a major proportion of the selectivity of the system, and 20 mS/cm is sufficient to suspend many such interactions, and substantially weaken all such interactions. It is to be understood however, that results may vary depending on the exact antibody being purified, and there may be value in conducting experiments at lower conductivity values. Reducing conductivity would appear to increase interference of the cationic solids with the interaction of a fatty acid and contaminating proteins, but could unexpectedly produce an improved overall result by increasing the ability of the cationic solids to bind soluble contaminants.

In one embodiment where functionalized solids are provided as particles, the particles may be equilibrated to a particular set of buffer conditions prior to introducing them to the fatty acid-containing harvest. As a general matter, the buffer used to equilibrate the particles may have approximately the same conductivity as the harvest, but achieved by simple inclusion of a sufficient concentration of sodium chloride to achieve that conductivity. Equilibration pH may vary depending on the results from simple experiments. One method step may be to equilibrate the particles to neutral pH with a low concentration of a buffering substance of appropriate pKa, where the buffer capacity of the equilibration buffer is insufficient to substantially alter the harvest. Another method step may be to select an equilibration pH close to the pH of the fatty acid-containing harvest, also where the concentration of the buffering species is very low, in this case so that it does not interfere with the neutralization of operating pH following performance of the method. Another method step may be to select an equilibration pH close to the desired pH of the harvest after treatment. Other approaches may be considered and are best evaluated experimentally. One skilled in the art will recognize that particle pre-equilibration may support a more controlled, reproducible process, and that the conditions can affect the overall results of the method. By the same token, the same considerations apply to equilibration of a device the fluid contact surfaces of which include insoluble charged multivalent chemically interactive moieties.

Given that methods disclosed herein provide IgG antibodies of such a high purity, it will be apparent that subsequent processing of the antibody to achieve higher levels of purification can be achieved by any further techniques normally employed in the art. Experimental data indicate that subsequent depth filtration step can reduce host protein contamination to less than 500 ppm and aggregates to less than 0.05%. Following depth filtration, concentration by tangential flow filtration can reduce host protein contamination to less than 50 ppm. From that point, an anion exchange chromatography step can reduce host protein contamination to less than 1 ppm.

Accordingly, in some embodiments there are provided methods of purifying an IgG antibody comprising contacting a cell culture harvest with at least one fatty acid having 7 to 10 carbon atoms to form a mixture, and contacting the mixture with one or more solids to form a mixture, wherein the one or more solids comprise a cationic functional group and a metal binding functional group, the metal binding functional group comprising a nitrogen-containing moiety selected from the group consisting of (1) a polyamine, (2) an imine, (3) an N-heterocycle, (4) an amino acid, (5) an N-hydroxyamide, (6), an arylamine, and combinations thereof, and separating solid materials after contacting the mixture with the one or more solids to provide a solution comprising the IgG antibody.

In some such embodiments, methods disclosed herein further comprise contacting the cell culture harvest with allantoin. In some embodiments, allantoin is present at a concentration in a range selected from the group consisting of: (a) from about 0.6 to about 30%, (b) from about 1 to about 10%, and (c) from about 1 to about 2%. In some embodiments, allantoin is in a range from a non-zero amount up to about 0.6%.

In one or more of the previous embodiments, a total amount of the one or more slid substrates bearing at least cationic and/or metal binding functional groups, is a volumetric proportion of the total volume of about 0.25%, 0.5%, 1%, 2%, 5%, 10%, 20%, or intermediate values in between. For the purpose of this numerical determination, the one or more solids refers to functionalized solids only and does not include any undissolved allantoin, should it be included in the methods. In one or more of the previous embodiments, the one or more solids comprises at least one functionality selected from the group consisting of hydrogen bonding, hydrophobic interactions, pi-pi bonding, van der Waals interactions, and combinations thereof.

In one or more of the previous embodiments where soluble functionalized substrates are employed, a total amount of the one or more such substrates bearing at least cationic and/or metal binding functional groups, is a volumetric proportion of the total volume of about 0.01%, 0.05%, 0.1%, 0.2%, 0.5%, 1.0%, 2.0%, or intermediate values in between. In some embodiments, a range for solid substrates may be from about 0.5 to about 5%, or about 1% to about 2%. In some embodiments, a range for soluble substrates may be from about 0.01 to about 1%, or from about 0.1 to about 0.5%. In one or more of the previous embodiments, the one or more soluble substrates comprises at least one functionality selected from the group consisting of hydrogen bonding, hydrophobic interactions, pi-pi bonding, van der Waals interactions, and combinations thereof.

In one or more of the previous embodiments, the at least one fatty acid and the one or more functionalize solid or soluble substrates are contained in a single vessel. In one more such embodiments, the at least one fatty acid and/or one or more functionalized solid or soluble substrates are added directly to the bioreactor in which the cell culture production process was conducted.

In one or more of the previous embodiments, solids are separated from the antibody-containing liquid in a device that permits the passage of fluid while preventing the passage of solid materials therethrough.

In one or more of the previous embodiments, the device that permits the passage of fluid while preventing the passage of solids therethrough comprises a porous material selected from the group consisting of a porous membrane, a monolith, a woven material, an amorphous fibrous material, a crystalline material, a hydrogelatinous material on a macroreticulate skeleton, a column of packed particles, and combinations thereof.

In one or more of the previous embodiments, methods disclosed herein further comprise contacting the solution with chemically functionalized solids disposed in a device.

In one or more of the previous embodiments, solid materials present after contacting a cell culture harvest with the at least one fatty acid or at the separating step, are removed by sedimentation or sedimentation following centrifugation.

In one or more of the previous embodiments, solid materials present after contacting a cell culture harvest with the at least one fatty acid or at the separating step, are removed by filtration. In some such embodiments, filtration comprises membrane filtration or depth filtration. In some such embodiments, the membrane filtration or depth filtration comprises a filter membrane that is functionalized. In some such embodiments, at least one functional group is electropositive. In some such embodiments at least one functional group binds metal ions.

In one or more of the previous embodiments, the first contacting step is preceded by partial purification of the IgG antibody.

In one or more of the previous embodiments, the cell culture harvest contains cells. In one or more of the previous embodiments, the cell culture harvest does not contain cells.

In one or more of the previous embodiments, the at least one fatty acid comprises a general structural formula of $CH_3(CH_2)_nCOOH$. In some such embodiments, the at least one fatty acid comprises enanthic (heptanoic) acid, or caprylic (octanoic) acid, or pelargonic acid, or capric (decanoic) acid. In some related embodiments, the fatty acid may contain a single double bond at any position of the fatty acid chain. In some such embodiments, the fatty acid containing the double bond is nonenoic acid. In some such embodiments, the fatty acid is 8-nonenoic acid. In some embodiments, the primary carbon chain may be unbranched; in others branched.

In one or more of the previous embodiments, the at least one fatty acid is present at a concentration in a range selected from the group consisting of: (a) from about 0.05 to about 5%, (b) from about 0.1 to about 1.0%, (c) from about 0.2 to about 0.4%, and (d) from about 0.1 to about 0.2%. In some embodiments, nonanoic acid may be used in a range from about 0.25 to about 0.50%. In some embodiments, nonenoic may be used in a range from about 0.2 to 0.4%.

In one or more of the previous embodiments, a cationic surfactant may be present at a concentration of: (a) from about 0.001 to 0.1%, (b) from about 0.005 to 0.05%, (c) from about 0.0125 to 0.025%. In one or more of the previous embodiments, a cationic surfactant may be cetyltrimethylammonium bromide.

In one or more of the previous embodiments, a hydrophobic cation component may be aromatic in nature, such as benzalkonium chloride, or chlorhexidine, or alexidine. In one such embodiment, the concentration of chlorhexidine may be in the range of: (a) from about 0.001% to 0.01%, (b) from about 0.005 to 0.05%, (c) from about 0.0075 to about 0.0125%.

In one or more of the previous embodiments, the one or more functionalized solid or soluble substrates comprises at least one charge configuration selected from the group consisting of anionic, cationic, or zwitterionic. In one or more of the previous embodiments, the one or more functionalized solid or soluble substrates comprises one species with the metal binding functional group and a separate species that is cationic. In one or more of the previous embodiments, the metal binding functional group is cationic.

In one or more of the previous embodiments, the metal binding functional group is selected from the group consisting of tris(2-aminoethyl)amine, diethylenetriamine, triethylenetriamine, tetraethylenepentamine, polypropylenimine tetramine, poly(amidoamine) (PAMAM) dendrimer, deferoxamine (desferioxamine), arginine, histidine, histamine, imidazole, and combinations thereof.

In one or more of the previous embodiments, the metal binding functional group is a compound of formula I:

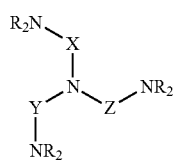

wherein each incidence of R is independently hydrogen or C1-C4 alkyl, with the proviso that at least one R is the site of attachment to a solid support, optionally via a linker; and each of X, Y, and Z are independently $(CH_2)_n$, where n is an integer from 2 to 6, wherein a $CH_2$ group is optionally replaced by O, or NH. In one such embodiment, the metal binding functional group is the cationic chelating agent is tris(2-aminoethyl)amine, TREN. In other embodiments, any close TREN analogue, in accordance with formula I may be used in methods disclosed herein. Numerous commercially available compounds are encompassed by formula I and other synthetic designed compounds may be readily prepared by methods routinely used by those skilled in the art. For example, a tertiary amine of formula I may be prepared from a primary amine by sequential reductive amination reactions.

In one or more of the previous embodiments, a dendrimeric layer of positive charges is constructed on a solid surface by successively activating the existing layer, for example by reductive amination, then introducing a multivalent amino species, washing away the unbound excess, then activating that surface again, etc. In the case of TREN for example, an initial layer of TREN is covalently attached to the membrane and the excess washed away. The bound TREN is then activated, the activation agent removed, and a fresh TREN introduced, with the effect of adding a TREN molecule on reactive amino groups at the termini of the originally immobilized TREN, with the effect of essentially doubling the depth of the charge field, and tripling the number of positively charged groups. After washing away unbound TREN, additional layers can be added. It will be understood by persons of ordinary skill in the art that many reagents and chemical methods may be employed to create conceptually equivalent arrangements of charges or other interactive groups.

In one or more of the previous embodiments, the one or more solids comprises one solid with the metal binding functional group and a separate solid that is anionic. In one or more of the previous embodiments, the metal binding functional group is anionic. In one or more of the previous embodiments, the metal binding functional group is selected from the group consisting of iminodiacetic acid, nitriloacetic acid, glutamic acid, aspartic acid, aminophenyl phosphate, and combinations thereof. In one or more of the previous embodiments, the anionic chelating agent is iminodiacetic acid.

In one or more of the previous embodiments, the one or more functionalized solid or soluble substrates comprises one species that is cationic and a separate species that is anionic.

In some embodiments, there are provided methods for purifying an IgG antibody comprising contacting a cell culture harvest with at least one fatty acid having 8 to 10 carbon atoms to form a mixture, contacting the mixture with allantoin; and separating solid materials after contacting the mixture with allantoin to provide a solution comprising the IgG antibody.

In some such embodiments, the methods further comprise contacting the solution with at least one chemically functionalized solid or soluble species. In some embodiments, the at least one chemically functionalized solid or soluble species comprises tris(2-aminoethyl)amine.

In one or more of the previous embodiments, allantoin is present at a concentration in a range selected from the group consisting of: (a) from about 0.6 to about 30%, (b) from about 1 to about 10%, and (c) from about 1 to about 2%. In one or more of the previous embodiments, allantoin is in a range from a non-zero amount up to about 0.6%.

In some embodiments, the method is applied to monoclonal or polyclonal IgG antibodies of natural origin, such as serum or plasma. In some embodiments, the method is applied to fragmentary immunoglobulin constructs of enzymatic or recombinant origin, such as Fab, $F(ab')_2$, or ScFv.

In some embodiments, there are provided kits to facilitate the practice of any one of the methods disclosed herein.

The following terms are defined so that the invention may be understood more readily. Additional definitions are set forth throughout the detailed description.

"Fatty acid" refers to an organic molecule consisting of a linear aliphatic chain terminated by a carboxyl group, with a general structural formula of $CH_3(CH_2)_nCOOH$, where n is an integer of at least one. For fatty acids suitable for practicing the present methods, "n" may be an integer of at least 4 up to 12. Specific examples of saturated fatty acids suitable for practicing methods particularly include enanthic (heptanoic, C7) acid, caprylic (octanoic, C8) acid, pelargonic (nonanoic, C9), and capric (decanoic, C10) acid. The term fatty acid may also refer to unsaturated fatty acids, containing one double bond, or a larger number of double bonds, such as 2, 3, 4, 5, and so on, which may occur at any position along the primary carbon chain.

"Allantoin" refers to a purine metabolite produced by oxidation of uric acid with a structural formula of $C_4H_6N_4O_3$ and an IUPAC name of 2,5-dioxo-4-imidazolidinyl urea.

"TREN" refers to Tris(2-aminoethyl)amine. This electropositive compound is particularly known to embody strong affinity for metal ions. It may be chemically affixed to various soluble and insoluble materials to endow those materials with chemical characteristics mediated by TREN.

"Cell culture" refers to the cultivation of cells in a liquid medium, in the present context, for the purpose of producing IgG monoclonal antibodies. Cells employed for this purpose commonly include Chinese hamster ovary (CHO) cells, but may include cell types from other mammals, as well as non-mammalian animal cells, plants, and microbes. In all cases, the liquid medium contains nutrients to support cell growth.

"Bioreactor" refers to a vessel within which cells are grown under controlled conditions. The vessel may comprise a stainless steel tank, or tank of other material, or a lined tank, or a polymer bag of dimensions suitable to grow the number of cells required to produce a target amount of the desired antibody; equipped with sensors and inputs to permit monitoring of critical process parameters and adjustments as necessary to maintain ideal conditions for cell growth and antibody production.

"Harvest" or "cell culture harvest" generally refers to the contents of a bioreactor at termination of cell culture process. In addition to the IgG produced, the harvest will initially contain cells, cellular secretions, and expelled contents of dead cells, as well as the contents of the nutrient medium in which the cells were originally grown. These non-antibody components constitute the contaminants that are to be removed from the antibody. The particularly include host protein and DNA, but may also include virus and endotoxin. Cell culture harvests also frequently contain misassembled or damaged forms of antibodies in fragmentary forms.

"Clarified cell culture harvest" refers to a harvest from which the cells have been removed. The clarification process may amount to no more than centrifugation, or microfiltration, or a combination of the two to remove solids, or it may include the use of chemical additives or solid materials bearing chemically interactive surfaces to extract particular classes of soluble contaminants from the harvest.

"Functionalized solid" or "one or more solids" refers to a chemically interactive solid in the physical form of a particle; membrane; monolith; filament or fiber; amorphous, woven, or crystalline frit; gel, or any compound construct or combination of such physical formats, including devices that embody one or more of such formats configured to support retention of solids while permitting liquids to pass through the device. The term functionalized itself is understood to indicate that base material is synthetically modified for the specific purpose of bearing an interactive chemical entity that enables the practice of the disclosed methods. Although un-dissolved allantoin crystals with chemically interactive surfaces may be present in various embodiments, it is to be understood that allantoin is not included within the scope of what is meant by "functionalized solids" since no modification of the natural material is required to render it functional. The same conceptual framework applies to functionalized soluble substrates, which may be used interchangeably or in combination with functionalized solid substrates. The soluble substrates, before functionalization, may be of natural or synthetic origin, and of a size ranging from a few hundred Daltons (D) to more than 100,000 D.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Host contaminant" or "Host cell contaminant" refers to biomolecules that are produced by the cells in which the product of interest is grown. The term may include various classes of host contaminants, such as host proteins and host DNA.

"Host protein" or "Host cell protein" or "HCP" refers to proteins that are produced by the cells in which the product of interest is grown. Such proteins represent one class of contaminants that are to be removed from the product of interest.

"Antibody" refers to an immunoglobulin of the class IgG, IgM, IgA, IgD, or IgE derived from human or other mammalian cell lines, including natural or genetically modified forms such as humanized, human, single-chain, chimeric, synthetic, recombinant, hybrid, mutated, grafted, and in vitro generated antibodies. The antibodies may be produced by a single clone, in which case they are referred to as monoclonal, or from more than one clone, in which case they are referred to as polyclonal. IgG antibodies particularly refer to a class of antibodies referred to as immunoglobulin G, which may also exist as one or a mixture of subclasses, for example in humans as $IgG_1$, $IgG_2$, $IgG_3$, or $IgG_4$; or in mice as $IgG_1$, $IgG_{2A}$, $IgG_{2B}$, or $IgG_3$; or in rat as $IgG_1$, $IgG_{2A}$, $IgG_{2B}$, $IgG_{2C}$. Antibodies produced naturally or recombinantly in eukaryotic hosts may exist in a variety of glycosylated forms, while antibodies produced in non-eukaryotic hosts may exist in a variety of glycosylated and non-glycosylated forms. The term antibodies is also understood to understood to include fragmentary constructs, whether of enzymatic or proteolytic origin, including but not limited to Fab, $F(ab')_2$, VHH, and ScFv.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

A useful starting point in customizing methods disclosed herein to a particular cell culture harvest is to add dry allantoin to cell culture harvest which contains cells or has had the cells already removed, where the added allantoin amounts to 1%, w/v. Mixing is maintained throughout the addition. A portion of the allantoin dissolves but another portion remains undissolved. In water, about 0.6% dissolves and the rest remains insoluble, but in complex biological systems where the allantoin interacts with various components, the proportions may shift. Nonanoic acid is added to a proportion of 0.3%, v/v, and stirring is continued. Fatty acid addition may alternatively take place in advance of allantoin addition, or concurrent with allantoin addition, but the suggested order appears to support slightly higher recovery of antibody from the treatment. It is unnecessary in some cases to adjust pH since the negatively charged carboxyl group on the fatty acid itself reduces the pH to about 5.4. In other cases, or if a salt of the fatty acid is used, then the pH of the harvest should be adjusted to about pH 5.2. Conductivity need not be adjusted. Mixing is maintained for up to 2 hours, or more, at which point polymer particles bearing TREN are introduced, where the proportion of particles may range from 2% to a 5% v/v. Amounts lower than 2% and higher than 5% tend to be less effective. Conductivity and pH need not be adjusted, but pH will increase spontaneously due to scavenging of nonanoate ions by the TREN particles. Mixing is continued for up to 4 hours, or more, then terminated. Different mixing methods, mixers, and mixing speeds vary substantially with respect to efficiency, and directly influence the quality of results obtained with the disclosed methods. They should therefore be investigated systematically before specifying a final method. After mixing, solids are optionally allowed to settle, and the liquid is clarified by any expedient method such as microfiltration or sedimentation. The clarified liquid may be optionally further treated by passage through a device with an internal liquid-contact surface populated by positive charges. No adjustment of pH or conductivity conditions is required at this step. The treated material may be evaluated for reduction of turbidity, host cell proteins, antibody aggregates, antibody fragments, DNA, histones, nucleosomes, virus, endotoxin, or other contaminants that may be pertinent to the goals of a particular purification.

In some embodiments, fatty acids may be introduced to the harvest in their acidic ionic form. When introduced in acidic form it may not be necessary to adjust the pH of the harvest since the fatty acid itself may titrate the working pH to a suitable value. pH may be adjusted, generally to a range of pH 4.0 to 6.0, but more ideally in a range of 4.5 to 5.5, or 4.8 to 5.2, or 5.2. More acidic conditions generally support better contaminant removal but less acidic conditions generally favor higher IgG recovery. As a general matter, the disclosed methods support good results at higher pH values than fatty acid precipitation as traditionally performed. It will be recognized that avoidance of extreme pH may reduce chemical stress imposed on the antibody and may provide secondary benefits in the form of higher recovery of functional antibody and/or improved antibody stability. Thus, it is generally beneficial to evaluate moderate pH values such as 4.5 to 5.5 as a matter of routine, despite contrary procedures commonly practiced in the art for conducting precipitation with fatty acids. Even where advance pH titration is not strictly required, it may be prudent since it may increase the reproducibility of the method. In other embodiments, fatty acids may be introduced as salts, such as sodium caprylate, or sodium pelargonate, or sodium caprate; or potassium caprylate, or pelargonate, or caprate, or other salt, such as with a potassium cation. When introduced as a salt, it will be necessary to adjust the pH of the working solution by addition of an appropriate titrating agent to achieve the desired working pH, since preparation of the salt effectively suspends the titrating capacity of the component ions. Suitable titrating agents may consist of acids or concentrated buffers pre-titrated to or near the target working pH. Preliminary comparisons indicate that the free acid forms support more effective contaminant removal than fatty acid salts.

Experimental data indicate that in some embodiments, capric acid is more effective than caprylic acid, especially for removal of aggregates, however, apparently due to its higher hydrophobicity, owing to its 10 atom carbon chain, it also involves higher risk of antibody losses, sometimes leading to lower recovery or erratic results from relatively minor variations in ambient temperature. Experimental findings to date indicate that the effective concentration range of capric acid is about half the concentration of caprylic acid in a similar context. This indicates 0.2% capric acid as one suitable concentration at which to begin experiments. Other experimental data indicate that pelargonic (nonanoic acid, 9-carbon) provides a more favorable balance of hydrophobicity and charge than either caprylic or capric acid, and supports more effective host protein reduction. Other experimental results indicate that 8-nonenoic acid, a 9-carbon fatty acid with a single double bond at the terminus of the fatty acid chain, also supports better results than caprylic or capric acid.

In some embodiments, functionalized solids may also be equilibrated to a particular pH value prior to their addition to the harvest. Such adjustment can be accomplished by washing the solids with a buffer containing about 100 mM NaCl at the target pH. The equilibrated solids may then be suctioned to remove excess liquid so that they can be added to the harvest as a moist cake. Experimentation may be beneficial to determine the most appropriate equilibration pH and conductivity for a given purification. In one embodiment, the solids may be pre-equilibrated in the first experiment to a pH of about 5.1 to 5.3, or 5.15 to 5.25, or 5.2 with 20 mM acetate, 100 mM NaCl. Higher and lower pH and conductivity values can be evaluated in subsequent experiments.

In some embodiments, functionalized soluble substrates may also be equilibrated to a particular pH value prior to their addition to the harvest. Such adjustment can be accomplished by adding acid or base to a liquid concentrate of the desired substrate(s). Modest experimentation may be beneficial to determine the most appropriate equilibration pH and conductivity for a given purification. In one embodiment, the soluble substrate(s) may be pre-equilibrated in the first experiment to a pH of about 5.1 to 5.3, or 5.15 to 5.25, or 5.2 with 20 mM acetate, 100 mM NaCl. Higher and lower pH and conductivity values can be evaluated in subsequent runs.

It will generally be worthwhile to evaluate a range of values for each variable in order to determine the most effective configuration for a particular purification. Allantoin concentration may be evaluated at a lesser proportion such as 1%, or a higher proportion such as 2, 3, 4, 5%, or intermediate increments. Experimental data indicate that allantoin becomes less effective below 1%, and that antibody recovery may be compromised above 5%, but broader ranges can be evaluated so long as there is an awareness of the potential compromise that may arise. Concentrations lower than the suggested 1% may particularly compromise aggregate reduction, while higher concentrations may compromise antibody recovery. Lower antibody recovery may be acceptable in some cases due to other effects deemed to be of greater value. Experimentation with incubation conditions for addition of allantoin alone is generally not needed, since experience indicates that its effects occur very rapidly. Fatty acid concentration may be varied from 0.05% to 5%. Incubation time as little as 15 minutes will likely compromise aggregate and host protein removal but may be evaluated along with 30 minutes, or 45 minutes, or 60 minutes, or 90 minutes, or 120 minutes, or other interval of choice. Incubation times longer than 2 hours may also be evaluated but experimental data to date do not reveal a significant advantage in such intervals. The proportion of functionalized solid or soluble substrates may be reduced below 2% or raised above that value. Lesser proportions appear to compromise overall effectiveness of the method, while higher concentrations tend to increase the expense without relative benefit. Higher concentrations also bear an increasing risk of binding the fatty acid to an extent where previously precipitated contaminants become resolubilized and re-contaminate the antibody-containing solution. Given the variation among cell culture materials, it will be prudent to initially explore a range of 1% to 5%. Incubation time is a major determinant of efficiency but should be balanced against the economic disadvantages of long process time intervals. 16 hours is convenient as a starting point because it corresponds with overnight incubation which can be conducted unattended, but lesser intervals should also be evaluated, such as 1 hour, 2 hours, 4 hours, and perhaps lesser, greater or intermediate intervals at the discretion of the user. Operating pH for the initial incubation with the fatty acid may range from 4 to 6, or 4.5 to 5.5, or 4.8 to 5.2. Conductivity generally does not require adjustment, but can be increased to about 2 times normal physiological conductivity by addition of a salt such as sodium chloride, or reduced by about half by addition of water, or wider ranges can be evaluated if desired.

It may be desirable to evaluate capric acid as an alternative to caprylic acid since experimental results indicate that it is more effective in some instances for removal of antibody fragments, and generally appears to be at least as effective in all other respects. Capric acid may be beneficially used at a temperature of at least about 30° C. to be soluble. This may be considered a disadvantage when applied to cell cultures harvests that are stored under refrigeration, but such concerns are suspended in situations where the fatty acid may be added directly to fresh cell culture harvest, and particularly where the cell culture harvest remains resident in the bioreactor. In the latter case, the high temperature may be maintained for any incubation interval desired. This approach may have the secondary advantage that if the temperature is reduced following the fatty acid incubation, some proportion of the capric acid will become insoluble and more likely associate with solids in the system, with the effect of increasing the efficiency of its removal from the system. Experimental data indicate that capric acid may be evaluated over the same range of concentrations as caprylic acid, though it will generally be found to be effective at a lower concentration, and the optimum concentration for pelargonic acid will generally be intermediate between the two. Carbon chain lengths less than 8 are less effective, particularly with respect to aggregate removal, and consequently require larger relative amounts, but remain potentially useful. Similarly, chain lengths greater than 10 are impaired by the difficulty of achieving high concentrations of soluble reagent due to the inherent solubility of the fatty acid, and they pose a higher risk of reduced antibody recovery in some instances. As a general matter, experimental data indicate that the more hydrophobic the fatty acid, the lower its effective concentration and the narrower its dynamic range. Other organic acids combining one or more negative charges and one or more aliphatic or aromatic hydrophobic moieties, including but not limited to saturated fatty acids, unsaturated fatty acids, polyunsaturated fatty acids, and phospholipids may also be used to practice methods disclosed herein, following the guidelines suggested herein.

Particles bearing TREN on their surface may be obtained by synthesis or purchased commercially, such as WORK-BEADS™ 40 TREN High (P/N 40 603 010) manufactured by BioWorks (Uppsala, Sweden). These particles are based on an agarose polymer, but it will be apparent that TREN may also be used to functionalize a wide range of solid and soluble substrates. Solids may be spherical, irregular, or filamentous, and may in some cases be soluble. The method may also be practiced in a format whereby TREN particles are packed in a column, or TREN is immobilized on a non-particulate surface such as a membrane, a monolith, a fiber, a crystalline matrix, or other solid support housed in a device that permits the passage of fluids, but not solids.

Solids bearing TREN may be substituted by materials bearing other chemical species, or accompanied by other materials bearing other chemical species, or both, where the other chemical species still serve the same function of particularly removing contaminants from IgG, and removing some proportion of the fatty acid previously added to the harvest. In one such embodiment, TREN particles are combined with particles bearing iminodiacetic acid. In another such embodiment, TREN particles are combined with particles bearing a butyl or other hydrophobic ligands on polymer particles with a negatively charged back bone. In another such embodiment, TREN particles are combined with particles bearing electronegative moieties such as sulfo-, phospho-, or carboxy-moieties. In another such embodiment, TREN particles are combined with a hydrophobic anion exchange material such as Dowex AG1x2 which comprises quaternary amines on a hydrophobic styrenedivinylbenzene backbone. In another such embodiment, TREN particles may be combined with a hydrophobic cation exchange material. In another such embodiment, TREN particles may be combined with more than one other type of particles. In another such embodiment TREN may be substituted by an electropositive material that, like TREN, embodies electropositivity accompanied by metal affinity and the ability to participate in hydrogen bonds and van der Waals interactions. In another such embodiment, TREN may be substituted by an electropositive species that also embodies the ability to participate in hydrogen bonding and van der Waals interactions. In one such embodiment where no electropositive species embodies a metal affinity functionality, a species may be present where a metal affinity functionality is provided by an electronegative or zwitterionic moiety. Electropositive species other than TREN may comprise one or more primary amines, one, or more secondary amines, or more tertiary amines, one or more quaternary amines, with some specific examples including but not limited to 1,3-Diamino-2-propanol; 2-Amino-1,3-propandiol; Ethanolamine; 1-Amino-4-guanidobutane; Ammonia; 1,2-Diaminoethane; 1,3-Diaminopropane; 1,3-Diamino-2-propanol; bis(TRIS)pentane; 1,2-Diaminoethane; Trimethylamine; bis(3-Aminopropyl)amine; 4-Amino-4-(3-hydroxypropyl)-1,7-heptanediol; 1,3-Diaminopropane; 2-Amino-2-methyl-1,3-propanediol; 1,2-Diaminoethane; Diethanolamine; tris(Hydroxymethyl)aminomethane; N-(3-Aminopropyl) diethanolamine; Ethanolamine; N-Butylamine; 1,3-Diaminopentane; 2-(2-Aminoethoxy) ethanol; Polyethylenimine (MW: 2000); 1-Amino-1-deoxy-d-sorbitol; tris(Hydroxymethyl)aminomethane; N,N-bis(2-hydroxyethyl)ethylendiamine; Pentaethylenhexamine; Triethanolamine; 1,3-Diamino-2,2-dimethylpropane; 3-Methylamino-1,2-propandiol; 2-Amino-ethanethiol; Diallylamine; Polyallylamine; Diethylenetriamine; N-Methyldiethanolamine; 1,5-Diaminopentane; 4-Amino-4-(3-hydroxypropyl)-1,7-heptanediol; 1,4-Diaminobutane; Trimethylamine; Diethyltriamine; 6-Amino-1-hexanol; tris(Hydroxymethyl) aminomethane; 2-(Methylamino) ethanol; Methioninol; 4-Amino-1-butanol; Hydrazine, arginine, lysine, histidine, and histamine.

In one embodiment, charged species that particularly embody a high degree of metal affinity may include but are not limited to Tris(2-aminoethyl)amine; Diethylenetriamine, triethylenetetramine, tetraethylenepentamine, polypropylenimine tetramine, PAMAM dendrimer (ethylenediamine core), deferoxamine, iminodiacetic acid, nitriloacetic acid, glutamic acid, aspartic acid, arginine, histidine, histamine, imidazole, aminoethyl phosphate, aminophenyl phosphate, or combinations thereof. It will be recognized that all of these embodiments are particularly directed to removal of chromatin and materials associated with chromatin, as a means of reducing the level of aggregates in a harvest. It will be equally recognized that these solid phase functionalities also play an important role in scavenging soluble contaminants from the harvest, and thereby contribute to the overall purification factor achieved by the method.

In embodiments where TREN and/or other chemical species are employed on a solid surface other than particles, the need to evaluate the time interval during which the particles are incubated with the harvest may be dramatically reduced. For example, where the chemical species may be present on the surface of filtration membranes through which the harvest may be flowed, the contact time may be on the order of minutes rather than hours. Other physical formats may impose different flow restrictions or lack thereof so that it will be prudent in all cases to evaluate the rate of fluid flow through the material. It will be equally prudent to evaluate materials that contain different amounts of solid phase surface contact area, and to evaluate the effectiveness of contact surface area versus flow rate, since larger area may support higher flow rate without compromising effectiveness, but may compromise economy. In embodiments employing TREN particles packed in a column, a useful starting point for experiments to optimize conditions will be to pack a bed height of not less than 5 cm, and flow harvest through the column at a linear flow rate of about 200 cm/hr. Columns with greater height, such as up to 30 cm may be used, and may support higher efficiency, but may also be used in conjunction with a reduced flow rate due to increased pressure drop across the greater bed height. As a general matter, columns of 5-15 cm bed height represent a suitable practical range. In most such embodiments, the volume of particles packed in the column, for the first experiment in a series, may be the same as the volume of particles that would be added directly to the harvest, such as 2%. Subsequent experiments may evaluate smaller or larger volumes, being mindful that smaller volumes may compromise effectiveness while larger volumes may compromise economy.

In some embodiments, it may be advantageous; after removing precipitates, to expose the treated supernatant to other functionalized solids to remove particular contaminant classes before continuing with other protein fractionation methods. In one such embodiment, the supernatant may be contacted with iminodiacetic acid functionalized particles. Experimental data indicate that TREN removes most metal ions more effectively than iminodiacetic acid, except for calcium, magnesium, and manganese which are removed more effectively by iminodiacetic acid. In another such embodiment, the supernatant may be contacted with hydrophobic anion exchange particles intended particularly to minimize the content of residual fatty acid. Experimental data indicate Dowex AG1X2, comprising quaternary amino groups on styrenedivinylbenzene particles as particularly suited to this purpose. In another such embodiment, either particles bearing a negatively charged metal binding functionality, or hydrophobic anion exchange functionality, or both, or neither, may be contacted with a filtration device, the surfaces of which may be functionalized with similar or alternative chemistries, or may not be functionalized. In one such embodiment, after removal of solids, the treated antibody preparation is passed through a depth filter bearing positive charges. In one such embodiment the conductivity of the protein preparation is reduced before being passed over the depth filter bearing charges to enhance binding of soluble acid contaminants. In one such embodiment, at least on sample-contact surface of the depth filter is chemically modified to make it electropositive. In one such embodiment, the depth filter may be substituted with an electropositive monolith, membrane, or porous-walled hollow fiber.

In some embodiments, it may be advantageous to conduct methods disclosed herein in which all of the disclosed elements are present, since the degree of influence asserted by the individual elements in the system as a whole cannot be predicted by their independent behavior. This highlights the point that the system as a whole achieves different results from conventional fatty acid treatments, through coordination with physical and chemical mechanisms that are distinct from fatty acid precipitation as practiced in the art. In practicing methods disclosed herein, single elements of the method may be serially executed to provide a streamlined approach for any particular target IgG antibody. In some embodiments, statistical techniques such as Design of Experiments (DoE), as known in the art, provide a means to identify a selection of a reduced number of method embodiments disclosed herein, designed to a particular IgG purification.

In one embodiment, the method may be applied to IgG-containing feed streams that have been processed previously by other means. In one such embodiment, a bioreactor harvest may have been treated in a manner distinct from the invention. It will be evident to a person of ordinary skill in the art that the presence of other chemical additives may compromise the effectiveness of the present method, or may be transparent, or that the present method may compound the beneficial effects of the previous treatment. In another such embodiment, the IgG-containing feed stream may be said to have been partially purified.

In some embodiments, the IgG to be purified may be monoclonal or polyclonal, and may reside in a biological fluid such as serum, or plasma, or other naturally-derived fluid. In such embodiments, the same method parameters may be evaluated over the same ranges as described for processing of monoclonal antibodies produced by in vitro cell culture techniques. It is to be expected that polyclonal antibodies cover a broader range of molecular behavior than a given monoclonal antibody, and that differences in behavior of antibodies derived from different species may be observed, but it will be within the purview of a person skilled in the art to adjust the elements of the methods disclosed herein without departing from the essential features of the invention as a whole.

In one embodiment, the harvest may be further processed by one or more methods after the treatment has been applied and solids removed from the system. One such embodiment may include passage of the treated harvest through a functionalized filter or other device equilibrated to the same conditions as the sample. In some such embodiments, the pH and conductivity conditions of the sample may be altered to enhance the ability of the functionalized device to extract contaminants. In another embodiment, the IgG may be concentrated and buffer exchanged by diafiltration, which will also remove some contaminants. In another embodiment, the treated harvest may be processed by high performance tangential flow filtration. In another embodiment, the clarified supernatant may be processed by cation exchange chromatography. In another embodiment, the IgG may be precipitated from the clarified harvest by polyethylene glycol. In another embodiment, IgG may be selectively precipitated from the clarified harvest by a kosmotropic salt such as ammonium sulfate, sodium sulfate, potassium phosphate, sodium citrate, or potassium citrate. In another embodiment, the clarified harvest may be processed by steric exclusion chromatography, where IgG is forced to accrete on hydrophilic particles in the presence of polyethylene glycol, or by preferential exclusion or chromatography, where the IgG is forced to accrete on particles in the presence of one or more kosmotropic salts. In another embodiment, the treated harvest may be processed by cation exchange chromatography. In another embodiment, the treated harvest may be processed by hydrophobic interaction chromatography. In another embodiment, the treated harvest may be processed by a form of so-called mixed mode chromatography, where a given chromatography medium comprises multiple chemical functionalities able to achieve different fractionation results than the constituent functionalities applied sequentially.

The following Examples are understood to be general, for illustration only, and should not be construed as limiting in any fashion. It will be evident to any person of skill that following an initial clarification/purification step that removes 99% of host protein contaminants, 90% of aggregates and fragments, 99% of DNA, endotoxin, and virus, almost any conceivable pair of follow-on polishing steps may be able to achieve IgG purity sufficient for in vivo human therapy, and is some embodiments, it may be possible to achieve this result with only a single follow-on processing step.

EXAMPLES

Example 1

Contaminant removal by caprylic acid precipitation in conjunction with treatment by functionalized particles. Different amounts of caprylic acid were added to cell culture harvest clarified by centrifugation, to final concentrations of 0.1, 0.2, 0.3, 0.4, and 0.5% respectively. Allantoin was added to each sample to a final concentration of 1%. Neither pH nor salt concentration was adjusted. Final pH at 0.4% caprylic acid was 5.4. The mixtures were stirred for 2 hours. Solids were removed by passing the sample through a 0.22 µm microfilter. The filtrate was then passed through a column containing an equal parts mixture of porous particles bearing TREN, iminodiacetic acid, and butyl ligands (WORKBEADS™ TREN 40 High from BioWorks, Chelex-100 from Bio-Rad, and Macro-Prep T-butyl from Bio-Rad, respectively), where the combined volume of particles was 5% of the applied sample volume. Host cell protein was reduced from an original 242,888 ppm of IgG in the harvest to 233,318 in 0.1% caprylic acid; 193,400 ppm in 0.2%; 57,519 ppm at 0.3%; 38,602 ppm at 0.4%; and 42,666 ppm at 0.5%. IgG fragments, including free light chain and light chain dimers were reduced from 12.2% in the harvest to 5.3% at 0.3% caprylic acid; 3.4% in 0.4%; and 3.6% in 0.5% caprylic acid. There was no fragment reduction at 0.1 and 0.2% caprylic acid. Aggregates were reduced from 1.28% in the harvest, to 1.22% in 0.1% caprylic acid, 0.87% in 0.2% caprylic acid, 0.31% in 0.3% caprylic acid, and were undetectable (less than 0.05%) at 0.4 and 0.5% caprylic acid. IgG recovery across the caprylic acid concentrations was 99% in 0.1% caprylic acid, 99% at 0.2%, 95% at 0.3%, 99% at 0.4%, and 95% at 0.5%. After treatment with the mixture of porous particles, host protein was reduced to 4205 ppm in the sample treated with 0.4% caprylic acid, representing a reduction of 98% and leaving the antibody at greater than 99% pure, with 1% fragments and no measurable aggregate, with an overall IgG recovery of 99%.

Example 2

The effect of operating pH on host protein reduction. A series of experiments was run where IgG-containing microfiltration-clarified harvest was treated with 0.4% caprylic acid; pH was not adjusted in an experimental control; pH was adjusted to pH 6 and 7 in two separate experiments. Host protein content was 38,602 ppm in the unadjusted control (pH 5.4), 171,232 at pH 6.0, and 243,675 ppm at pH 7.0.

Example 3

Subsequent purification by IgG precipitation with polyethylene glycol. The samples from Example 1 treated with 0.4% and 0.5% caprylic acid, followed by the porous particle treatment, were further purified by precipitation with polyethylene glycol (PEG-6000), conducted at 20.5% PEG, 800 mM NaCl, 50 mM Hepes, pH 7.0. After PEG precipitation of harvest treated with 0.4% caprylic acid, host proteins were reduced to 11 ppm, aggregates to 0.09%, and light chain fragments were undetectable. After PEG precipitation of harvest treated at 0.5% caprylic acid, host protein was reduced to 13 ppm, aggregates to 0.1%, and light chain fragments were undetectable. These results both correspond to a 99.9995% reduction of host protein. In a parallel control experiment where the harvest was not treated by the present method, PEG precipitation reduced host protein to 67,687 ppm. The more than 6,000-fold improvement provided by the disclosed method illustrates two distinct benefits. The obvious benefit is that reduction of host protein contamination by the present method permits a follow-on method to achieve a yet greater reduction of host protein contamination. It also highlights the arguably greater benefit that the disclosed method particularly removes contaminants that interfere with the ability of the purification method itself to achieve its best results.

Example 4

Integration of the method with an anion exchange depth filter. 0.4% caprylic acid was added to cell culture harvest without any pre-treatment. Allantoin was added to a final concentration of 1%. The mixture was continuously stirred for 2 hours, then passed through a two-stage anion exchange depth filter instead of a membrane microfilter as in Examples 1-3, in preparation for the same porous particle mixture treatment described in Example 1. The depth filtration step reduced host protein 19-fold from 176,244 ppm to 9173 ppm, reduced aggregates from 2.03% to undetectable (less than 0.05%); and reduced light chain contaminants from 12% to 1%.

Example 5

Enhanced performance by protein A affinity chromatography. A sample prepared by the treatment with allantoin, caprylic acid, and mixed particles as described in Example 4 was subjected to purification by protein A affinity chromatography (ToyoPearl AF-rProtein A 650F, Tosoh Bioscience). Protein A normally reduces contaminating host protein levels to the range of 500 to 2,000 ppm of IgG when feed stream consists of cell harvest clarified by centrifugation and/or microfiltration. Performing the caprylic acid-allantoin and porous particle method described in Example 1, in advance of protein A, allowed the protein A step to achieve a host protein level below 1 ppm, and aggregates beneath the level of detectability. This particularly highlights that the disclosed method removes contaminants that interfere with the ability of protein A to fulfill its potential.

Example 6

Enhanced performance by cation exchange chromatography followed by anion exchange chromatography. A sample prepared by the treatment with allantoin, caprylic acid and mixed particles as described in Example 4 was subjected to further purification by cation exchange chromatography. Cation exchange normally achieves host protein levels of 5,000-15,0000 ppm when applied after cell harvest clarification by centrifugation and/or microfiltration. At least two additional chromatography steps are typically used to achieve levels lower than 100 ppm. Performing the disclosed method in advance of cation exchange allowed the cation exchange step to achieve a host protein level of 4.6 ppm, and reduced aggregates to 0.68%. A single follow-on polishing step of anion exchange in void exclusion mode in 50 mM Tris, pH 8.25 reduced host protein to less than 1 ppm and aggregates to 0.53%. Alternatively, a final polishing step of Capto adhere chromatography, where the column was equilibrated to 1.0 M NaCL, 50 mM Hepes, pH 7.0, loaded, washed with the same buffer, then eluted with a linear gradient to 300 mM NaCl, 50 mM Hepes, pH 7.0 reduced host protein contamination to less than 1 ppm and aggregates to less than 0.05%.

Example 7

Enhanced performance by antibody precipitation followed by anion exchange chromatography. A sample prepared by treatment with allantoin, caprylic acid and mixed particles as described in Example 4 was subjected to further purification by a mixed-mode precipitation step, initially with PEG as described in Example 3, followed by a transition to 2.0 ammonium sulfate, pH 7.0. The IgG was resolublized and tested revealing 5.9 ppm host cell protein. Aggregates were beneath the level of detection (less than 0.05%). A single follow-on polishing step of anion exchange in void exclusion mode in 50 mM Iris, pH 8.25 reduced host protein to less than 1 ppm. This result is important because it highlights the ability of the disclosed method to provide a foundation that permits inexpensive low-functioning fractionation methods to achieve better overall purification performance that processes that are based on the perceived highest performing fractionation method of all: protein A affinity chromatography.

Example 8

Replacement of multiple species of mixed particles with TREN particles 0.5% caprylic acid was added to cell culture harvest without any pre-treatment. This produced a pH of about 5.3. The mixture was continuously stirred for 2 hours. Allantoin was then added at 1% and incubated for 15 mins. TREN particles (Workbeads TREN 40 high) were added at a proportion of 5% v/v and incubated overnight at room temperature. Half of the volume was passed through a depth filter as above to remove solids. The other half was passed through a 0.22 µm microfilter. The microfiltration version produced material that contained 100-fold less host protein than the harvest (1,758 versus 176,244 ppm), aggregates from 3.03% to 0.83%, and antibody fragments from 11.8 to 1.23%, with an antibody recovery of 90%. The depth filtration version reduced host protein to 135 ppm and aggregates to less than 0.01%, with an antibody recovery of 85%.

Example 9

Particle incubation time. A series of experiments was run in parallel to Example 8. Reducing incubation time with the TREN particles to 4 or 6 hours produced roughly the same results as overnight (16 hour) incubation. Reducing incubation time to 1 or 2 hours achieved inferior results.

Example 10

IgG purification of treated harvest by concentration/diafiltration, followed by anion exchange chromatography. Tangential flow filtration is commonly used for concentrating and diafiltering process solutions, but it is not considered to be a purification step because its abilities are considered to be too limited. The material processed with depth filtration from Example 8 was concentrated by tangential flow filtration. Host protein concentration was reduced to 20 ppm. Aggregates remained at 0%. This material was polished by anion exchange in void exclusion mode as described in Example 6. Host protein was reduced below the level of detectability (less than 60 parts per billion). Aggregates were undetectable. Antibody light chain fragments and heavy chain fragments were undetectable. This highlights the ability of the disclosed method to enable another perceived low-functioning fractionation technique to achieve higher purity than processes based on protein A chromatography as typically practiced.

Example 11

IgG purification by precipitation and anion exchange chromatography. The material processed with depth filtration from Example 8 was concentrated by the precipitation method in Example 7, then the anion exchange method in Example 6. Host protein concentration was reduced to less than 1 ppm at the precipitation step and beneath the level of detectability (less than 60 parts per billion) after anion exchange. Aggregates were undetectable. Antibody light chain fragments and heavy chain fragments were undetectable. This highlights the ability of the disclosed method to enable another perceived low-functioning fractionation technique to achieve higher purity than processes based on protein A as typically practiced.

Example 12

Enhancement of IgG purification by protein A affinity and anion exchange chromatography. The material processed with depth filtration from Example 8 was fractionated by the protein A affinity and anion exchange steps as in Example 6. Host protein concentration was reduced to less than 1 ppm at the protein A step and beneath the level of detectability (less than 60 parts per billion) after anion exchange. Aggregates were undetectable. Antibody light chain fragments and heavy chain fragments were undetectable. This example highlights the ability of the disclosed method to enhance the performance of a high-functioning purification method by more than 100-fold.

Example 13

The disclosed method as an intermediate purification step. An experimental control was run in which cell culture harvest clarified by centrifugation and microfiltration was fractionated by precipitation as described in Example 7. This reduced host protein from 287,655 ppm to 67,687 ppm, aggregates from 2.83 to 1.57%, and antibody fragments from 10.4 to 2.3%. A follow-on anion exchange step in void exclusion mode reduced host protein 99.6% to 221 ppm and aggregates to 1.45%. This experimental control was compared with a process in which the precipitation step was followed by treatment with 0.4% caprylic acid, 1% allantoin, and 5% TREN-functionalized particles. After incubation for 6 hours, solids were removed by depth filtration. Host protein contamination was reduced to 21 ppm and aggregates below the level of detectability. This material was fractionated by anion exchange chromatography as described in Example 6. Host protein contamination was reduced below the limit of detectability. Thus using the disclosed method as an intermediate step increased the purity of the final product by greater than a factor of 200.

Example 14

Qualification of capric acid and enablement of an ammonium sulfate precipitation, anion exchange chromatography purification process. Cell culture supernatant was treated with 0.2% capric acid, 1% allantoin and 5% TREN particles. After overnight incubation at 37° C., solids were removed by depth filtration on a Sartorius PC-1 filter. The filtrate was then purified by precipitation with 2.0 M ammonium sulfate in 50 mM phosphate, pH 7.0, then by a final polishing step of anion exchange chromatography in void exclusion mode as described in example 6. Host protein was reduced from an initial level of 287,655 ppm to 987 ppm by the capric acid-allantoin-particle treatment, then to 76 ppm by ammonium sulfate precipitation, and less than 1 ppm by anion exchange. Aggregates were reduced beneath the level of detection at the capric acid-allantoin-particle step. Antibody light chain and heavy chain fragments were reduced from 10.4 to 0.6% at the capric acid-particle step, and beneath the level of detectability after ammonium sulfate precipitation. This provides another example where the disclosed method enables a perceived low-functioning ammonium sulfate precipitation step to achieved better purification than the perceived high-functioning alternative of protein A affinity chromatography as typically loaded with harvest clarified by physical means.

Example 15

Evaluation of capric acid concentration. Experiments were run in parallel with example 14 at 0.1, 0.4 and 0.6% capric acid. 0.1% did not support comparable purification. 0.4% and 0.6% caused excessive antibody loss. An experiment with 1% capric acid precipitated nearly all of the antibody with the contaminants.

Example 16

Evaluation of different caprylic acid concentrations with and without allantoin. Cell-containing harvest was clarified by centrifugation and membrane filtration through a 0.22 micron membrane, then the pH of the supernatant was reduced to 6.0. Various subsamples were treated with caprylic acid at amounts of 0.01%, 0.05%, and 0.1%. All samples were turbid following treatment, indicating the persistence or reformation of particulates, even after precipitated materials were removed by centrifugation. The same series of experiments was repeated in the presence of 2% allantoin. Antibody recovery and reduction of contaminants was essentially equivalent but the processed material was sparkling clear after processing. This Example illustrates the contribution of allantoin to the performance of the disclosed method as a whole.

Example 17

Accelerated clarification of mammalian cell harvest by addition of allantoin. Allantoin was added to a final concentration of 1% to 5 L of cell-containing cell culture harvest containing an IgM monoclonal antibody, among the usual spectrum of contaminants. The container was swirled gently to mix the components. Interactions between allantoin and unknown cell culture components caused this amount of allantoin to be fully dissolved, so an additional 1% was added, bringing the total added amount to 2% (w/v). The container was again swirled to mix the components. Whereas particulate materials had been observed to settle very slowly before addition of allantoin, and only slightly faster in the presence of 1% allantoin, settling rate was obviously accelerated by 2% allantoin, and left the cell culture supernatant sparkling optically clear within a period of about 20 minutes. The differential between 1% and 2% allantoin was interpreted as an indication that 1% allantoin, by virtue of the presence of some solubilizing substances in the sample, was almost completely dissolved. The supernatant was subsequently decanted. This inadvertently resuspended a portion of the precipitate, which was subsequently centrifuged to sediment the remaining solids. This highlights the ability of allantoin to improve the quality of cell harvest clarification independent of fatty acids or other additives. It also highlights the potential benefit of conducting initial trials with an allantoin concentration of at least 2%. It further highlights the important point that the solubility of allantoin may be affected by components of a sample, with the effect that a supersaturating concentration of allantoin can be determined experimentally, although its known solubility in water may provide a useful preliminary guide.

Example 18

Clarification of an *E. coli* lysate by addition of allantoin. 20 grams of *E. coli* paste in 250 mL of 50 mM Hepes, pH 7.0 past was homogenized with a microfluidizer at 16,000× g. The homogenate was then centrifuged at 15,000×g for 1 hour to remove the largest particulate species. This produced a tan-colored turbid supernatant. Dry allantoin was added directly to the supernatant to a final concentration of 5% w/v. The mixture Was swirled for about 1 minute than allowed to settle. Insoluble materials settled within a few minutes leaving a sparking clear supernatant that contained more than 90% of the protein product that was present in the original homogenate. The supernatant passed easily through a 0.22 micron membrane filter, where supernatant prior to allantoin treatment clogged the filter virtually on contact. This Example highlights the ability of allantoin to dramatically improve the filterability of a treated sample, and highlights the independent contribution of allantoin to the performance of the method as a whole. It also illustrates that the disclosed method is not restricted to antibodies grown by mammalian cell culture.

Example 19

Recovery of antibody and endotoxin reduction from an IgG-endotoxin mixture using allantoin. Endotoxin was added to 1 mg/mL human IgG in 5 mM HEPES 100 mM NaCl pH 7.0 to 22,000 EU/ml. 2% (w/v) allantoin was added to aliquots of this mixture and allowed to mix for 15 minutes at room temperature. The suspension was clarified by centrifugation. Protein and endotoxin concentrations were measured to calculate antibody recovery and endotoxin removal. 2% (w/v) allantoin reduced endotoxin twofold. Antibody recovery was unaffected by the amount of allantoin. In a subsequent series of experiments, the amount of allantoin was increased in increments, up to 10%. Antibody recovery diminished gradually to about 93% at 10% allantoin, while endotoxin removal efficiency increased to about 99%. These experiments illustrate that the use of larger amounts of allantoin can result in a loss of IgG. Additional experiments with proteins ranging in size from about 12 kDa to 1 MDa indicated a definite trend whereby the loss of protein increases with increasing protein size. This Example illustrates the ability of allantoin to enhance the performance of the disclosed method as a whole.

Example 20

A viral culture containing $10^{10}$ particles per mL of minute virus of mice was copreciptitated under physiological conditions by addition of allantoin in an amount of 10%. Infectivity testing of the supernatant documented removal of 99.9% of the virus. Another viral culture containing $10^{10}$ particles per mL of murine leukemia virus was co-precipitated under physiological conditions by addition of allantoin in an amount of 10%. Infectivity testing of the supernatant documented removal of 99.9% of the virus. This Example illustrates the independent contribution of allantoin to the disclosed method as a whole.

Example 21

Clarified IgM cell culture harvest with NaCl added to a conductivity of 20 mS/cm was passed through TREN particles packed in a column. IgM recovery was 98%. Histone and general host protein removal were about 35%. DNA removal was 99%. High molecular weight aggregates were reduced from 19.4% to 1.3%. This Example illustrates the independent contribution of TREN particles to the disclosed method as a whole.

Example 22

Anti-HER2 IgG cell culture harvest clarified by centrifugation and microfiltration was passed through TREN particles packed in a column, where the volume of TREN particles was 2% of the volume of applied cell culture harvest. Flow rate was 200 cm/hr. The treatment reduced aggregates from 20.4% to less than 3.2%. Host protein contamination was reduced by 58%. This Example illustrates the independent contribution of TREN particles to the disclosed method as a whole.

Example 23

Anti-HER2 IgG cell culture harvest clarified by centrifugation and microfiltration was passed through a column packed with the same mix of particles as Example 1, where the volume of the particles was 2% of the volume of applied cell culture harvest. Flow rate was 200 cm/hr. The treatment reduced aggregates from 17.4% to less than 4%. Host protein contamination was reduced by 42%. This example illustrates the independent contribution of mixed functionalized particles to the disclosed method as a whole.

Example 24

Comparison of metal removal selectivity of TREN and iminodiacetic functionalities. Cell culture harvest clarified by centrifugation and microfiltration was passed over either a column of TREN-functionalized agarose polymer microspheres, or a column of Chelex-100. Results in Table 1 shows that Chelex is substantially more effective for calcium and magnesium. The two are similarly effective for copper, manganese, nickel, lead, and zinc. TREN is substantially more effective for aluminum and iron.

TABLE 1

| ICP-OES metal analysis. | | | | | | | | | |
| --- | --- | --- | --- | --- | --- | --- | --- | --- | --- |
|  | Al | Ca | Cu | Fe | Mg | Mn | Ni | Pb | Zn |
| Original material | 55 | 20,824 | 11 | 5590 | 35,255 | 10 | 17 | 8 | 653 |
| Post-Chelex | 33 | 88 | 5 | 967 | 3 | 2 | 6 | nd | 256 |
| Post-TREN | 10 | 15,709 | 4 | 255 | 23,954 | 4 | 8 | nd | 262 |

All values in ppm.
nd = not detected.

Example 25

Integrated purification of monoclonal IgG from cell culture harvest. Cell-containing anti-HER2 cell culture harvest was combined with allantoin at a final concentration of 2%, and caprylic acid at a final concentration of 0.2%, then incubated for 2 hours. TREN-functionalized particles were added to a final proportion of 5%, and the mixture was allowed to incubate for an additional 4 hours. Precipitates were removed by centrifugation and the supernatant was combined with an equal mixture of Chelex-100 and Dowex AG1x2 particles, where the combination was at a final proportion of 2%. After 1 hour incubation, the mixture was applied to an anion exchange depth filter to remove the particles. The filtrate was subsequently concentrated in a tangential flow ultrafiltration system using a membrane with a porosity equivalent to a globular protein size of about 50 kDa, and diafiltered against a buffer of 1 M NaCl, 1 M sorbitol, 20 mM EDTA, 50 mM phosphate, pH 7.2. After concentration to about 20 g IgG per liter, the retentate was processed by anion exchange chromatography on a column of UNOsphere Q operated in void exclusion mode. This example illustrates the ability of the disclosed clarification methods to enable process performance far in excess of current methods despite using only a perceived low-functioning purification method (ultrafiltration) and a single anion exchange chromatography step. Process results are summarized in Table 2.

TABLE 2

Process summary.

| Step | parameter | | | |
|---|---|---|---|---|
| | HCP ppm | HCP rdx | Aggr. % | Recov. % |
| Original material | 276,008 | 0 | 10.47 | 100/100 |
| Post-clarification | 112 | 99.96 | 0.02 | 91/91 |
| Post-ultrafiltration | 7.1 | 99.997 | 0.03 | 96/87 |
| Post-VEAX | 0.06 | 99.99998 | <0.01 | 99/86 |

HCP: host cell protein.
HCP rdx: % reduction.
nd: not detected.

Example 26

Antagonism between fatty acids and oppositely charged solids. Cell harvest clarified by centrifugation and microfiltration was treated with 1% allantoin and 0.4% caprylic acid, then incubated for 4 hours. The material was split into 3 aliquots. The first was treated with 5% TREN particles. This was the experimental control for the series. The second was treated with 10% TREN particles. The third was treated with 5% TREN particles and 2% Dowex AG1X2 particles. As in other experiments under these conditions, the combination with 5% TREN particularly reduced free light chain contaminants to less than 0.1%. The amount of free light chain rebounded however to more than 5% in the experiment with 10% TREN and TREN plus Dowex. These results indicate that the solid materials removed a sufficient amount of caprylic acid from precipitated light chains for them to regain solubility and thereby recontaminate the unprecipitated IgG. It is especially notable that a lesser amount of Dowex was able to achieve this result compared to TREN. This is consistent with the known strong hydrophobicity of this particular form of Dowex, which should elevate its effectiveness, for competitively dissociating caprylic acid from caprylic acid-contaminant precipitates.

Example 27

Antagonism between fatty acids and oppositely charged solids. Cell harvest clarified by centrifugation and microfiltration was treated with 1% allantoin and 0.4% caprylic acid, then incubated for 4 hours. The material was split into 2 aliquots. The first was treated with 5% TREN particles. This was the experimental control for the series. The second was treated with 5% TREN particles and 5% chelex 200 particles. As in other experiments under these conditions, the combination with 5% TREN particularly reduced free light chain contaminants to less than 0.1%. The amount of free light chain rebounded however to more than 5% in the experiment with TREN+Chelex. This is difficult to explain since both TREN and chelex are solid phase chelators, and Chelex is negatively charge, which means that it should not interact directly with caprylate ions, and should therefore have no effect on the ability of TREN to remove light chain. These results suggest that the effect of solid phase chelators in the system may not be mediated by metal binding, but by a chemical feature of such ligands that parallels but is distinct from metal binding.

Example 28

Altered process order. Anti-HER2 cell culture harvest was treated with 1% allantoin and 0.4% caprylic acid for 2 hours, then 5% TREN particles for 4 hours. Solids were removed by centrifugation and the supernatant passed over an anion exchange depth filter (Sartorius DC-1). Host cell protein contamination was reduced to 531 ppm. Aggregates were reduced to less than 0.1%. Excess free light chain was reduced to less than 1%. In a related experiment, the depth filter was substituted by an anion exchange hollow fiber (Qyu-speed, Asahi). Host protein reduction was equivalent, to 528 ppm, but aggregates were reduced to only 3.7%.

Example 29

Non-interactivity of DNA and fatty acids. Caprylic acid precipitation has been described as having the ability to precipitate DNA (Brodsky et al supra). This does not make sense because their identical negative charges should repel each other. This was confirmed in an experiment in which purified DNA at concentrations of 1 2, 5, an 10 micrograms per mL was combined with 0.4% caprylic acid at pH 5.2 and physiological conductivity for 2 hours. No significant differences were observed in the DNA concentrations after treatment. This shows that apparent DNA binding described by others is attributable to indirect binding through an intermediate species, which according to research by Gan et al (supra), is likely the histone component of nucleosomes.

Example 30

Contaminant reduction by caprylic acid precipitation in the absence of features of the disclosed method. Experiments were run to document a baseline for clarification performance by caprylic acid, to illustrate the differences between caprylic acid alone, and the disclosed method. All experiments were conducted on an IgG-containing cell culture harvest containing 259,777 ppm host protein and aggregates amounting to about 30% of the non-aggregated IgG. All experiments were conducted at physiological, conductivity. Effects on host protein, IgG recovery, and aggregate content were evaluated at 0.5 pH unit intervals from 3.5 to 7.0. Highest host protein reduction was at pH 3.5, but IgG recovery was less than 50%. Highest aggregate removal was at pH 4.5. Highest IgG recovery was at pH 6.5 and 7.0, but host protein and aggregate reduction were poor. Complete results are given in the table below.

| pH | Host proteins (ppm) | IgG recovery (%) | Aggregate (%) |
|---|---|---|---|
| CCH | 260k | 100 | 23.7 |
| 3.5 | 56.6k | 46 | 7.9 |
| 4.0 | 78.3k | 43 | 3.2 |
| 5.5 | 90.4k | 76 | 2.9 |
| 5.0 | 102k | 83 | 4.1 |
| 5.5 | 115k | 89 | 5.1 |
| 6.0 | 257k | 94 | 15.8 |
| 6.5 | 246k | 100 | 16.6 |
| 7.0 | 266k | 105 | 16.6 |

Example 31

The effect of pH on the disclosed method. An IgG-containing harvest also containing 172,038 ppm host protein and 22% aggregates was evaluated at pH values of 5.0, 5.5, 6.0, 6.5, and 7.0, where 1% allantoin and 4% caprylic acid were added to the harvest and mixed gently, then 5% (v/v) BioWorks TREN high particles were added and mixed for 4 hours before removing the solids by centrifugation and microfiltration. Results were dramatically superior to Example 30, highlighting the superior performance of the disclosed method. Complete results are given in the table below. FLC refers to free light chain.

| pH | Host proteins (ppm) | IgG recovery (%) | Aggregate (%) | FLC (%) |
|---|---|---|---|---|
| CCH | 172k | 100 | 23.7 | 23.7 |
| 5.0 | 1529 | 84 | 0.3 | 0.4 |
| 5.5 | 1198 | 95 | 0.3 | 0.7 |
| 6.0 | 6595 | 99 | 0.4 | 18.5 |
| 6.5 | 59k | 94 | 0.5 | 19.8 |
| 7.5 | 62k | 94 | 0.5 | 20.2 |

The previous experiment was repeated at narrower pH intervals to refine the estimate of optimum pH. These experiments were performed on a different cell culture harvest containing the same antibody. Complete results are described in the following table.

| pH | Host proteins (ppm) | IgG recovery (%) | Aggregate (%) | FLC (%) |
|---|---|---|---|---|
| CCH | 195k | 100 | 22.9 | 23.6 |
| 4.8 | 3708 | 80 | 0.3 | 0.3 |
| 5.0 | 1469 | 86 | 0.2 | 0.2 |
| 5.2 | 1169 | 91 | 0.3 | 0.3 |
| 5.4 | 1476 | 94 | 0.4 | 0.3 |
| 5.6 | 5820 | 97 | 0.5 | 12.4 |
| 5.8 | 36k | 97 | 0.5 | 17.8 |

Example 32

The combined influence of pH and conductivity in the absence of the functionalized particle addition. A series of experiments was conducted, evaluating the effects of pH 4.8, 5.2, and 5.6, each at conductivity values of 12 mS/cm, 16 mS/cm, and 20 mS/cm. The starting material was a cell culture harvest containing the same antibody, plus 213,821 ppm host protein, and 25.6% aggregates. The data show that the disclosed method, even limited to the allantoin and caprylic acid components, achieves substantially better results than caprylic acid alone (Example 30). Complete results are described in the following table.

| pH/cond. | Host proteins (ppm) | IgG recovery (%) | Aggregate (%) | FLC (%) |
|---|---|---|---|---|
| CCH | 195k | 100 | 22.9 | 23.6 |
| 4.8 | | | | |
| 12 | 4556 | 79 | 1.0 | 0.4 |
| 16 | 5977 | 89 | 3.0 | 0.3 |
| 20 | 7433 | 89 | 3.0 | 0.7 |
| 5.2 | | | | |
| 12 | 2237 | 92 | 0.9 | 0.2 |
| 16 | 4340 | 100 | 1.8 | 0.9 |
| 20 | 4937 | 101 | 0.9 | 0.8 |
| 5.6 | | | | |
| 12 | 9679 | 100 | 0.8 | 14.5 |
| 16 | 35k | 100 | 0.8 | 17.0 |
| 20 | 44k | 100 | 0.9 | 14.1 |

Example 33

Comparison of commercially available TREN particles with experimentally prepared TREN particles. Commercial TREN particles are manufactured to perform the technique of immobilized metal affinity chromatography and embody physical properties not necessary to practice the disclosed method, such as pressure resistance, defined homogenous particle size distribution, and defined pore size distribution in the particles. Besides being unnecessary, these features make the particles expensive. We prepared TREN particles from cheap biodegradable cellulose particles and cellulose fibers. The particles or fibers were equilibrated with 1 M NaoH, 1 mM sodium borohydride, 100 mM tris(2-aminoethyl)amine (TREN), and 320 mM epichlorohydrin, then allowed to react for 4 h at 50 degrees C. The buffer was replaced with 1 M NaCl, then water, to wash away residual reactants and reaction byproducts. Immobilization of TREN was confirmed by binding of the anionic dye Methyl Blue. The experimental particles were compared with commercial TREN particles at 5% v:v following treatment of the harvest with 1% allantoin and 0.4% caprylic acid at pH 5.2. IgG-containing cell culture contained 28.3% aggregates and 258,999 ppm host proteins. Complete results are presented in the following table. cTREN refers to commercial TREN (BioWorks TREN high) CP refers to cellulose particles. CF refers to cellulose fibers. 1% experimental particles outperformed 1% commercial TREN, but 5% commercial TREN gave better performance than 5% experimental particles.

| Particles | Host proteins (ppm) | IgG recovery (%) | Aggregate (%) | FLC (%) |
|---|---|---|---|---|
| CCH | 259k | 100 | 28.3 | 29.1 |
| 5% cTREN | 1377 | 83 | 2.2 | 1.8 |
| 1% cTREN | 14k | 91 | 2.7 | 10.1 |
| 5% CF | 30k | 89 | 2.9 | 21.1 |
| 1% CF | 8750 | 86 | 1.8 | 11.8 |
| 5% CP | 4802 | 90 | 1.8 | 5.9 |
| 1% CP | 6629 | 88 | 4.7 | 2.1 |

Example 34

Comparison of the disclosed method with the addition of activated carbon particles. The method was applied to IgG-containing cell culture harvest containing 282,773 ppm host proteins and 33.4% aggregates. The harvest was treated with 0.4% acrylic acid and 1% allantoin, plus 0, 1, 2, or 4% activated carbon (4-12 mesh, Darco). Activated carbon addition decreased host protein, but disproportionately decreased antibody recovery. Activated carbon also catastrophically and without warning eliminated all protein from the sample, including IgG, at 4%. Results are presented in the following table.

| AC % | Host proteins (ppm) | IgG recovery (%) |
|---|---|---|
| CCH | 283k | 100 |
| 0% AC | 10k | 91 |
| 1% AC | 7259 | 86 |
| 2% AC | 6408 | 80 |
| 4% AC | none detected | none detected |

Example 35

The influence of particles functionalized with different positively charged species. The effects of commercial TREN at 1, 2, 3, 4, and 5% (v:v) were compared with Dowex AG1X2 at the same levels. The experiment was performed with IgG-containing harvest that also contained 188,503 ppm host proteins and 26.4% aggregates. In brief, Dowex supported slightly better recovery and aggregate removal, but host proteins and free light chain were removed more effectively by TREN. Results are presented in the following table.

| TREN/Dow. | Host proteins (ppm) | IgG recovery (%) | Aggregate (%) | FLC (%) |
|---|---|---|---|---|
| CCH TREN | 186k | 100 | 26.4 | 24.2 |
| 1% | 7216 | 91 | 7.9 | 0.9 |
| 2% | 4147 | 89 | 2.7 | 0.7 |
| 3% | 3342 | 90 | 2.2 | 0.5 |
| 4% | 2966 | 94 | 1.3 | 0.7 |
| 5% | 2275 | 91 | 1.6 | 0.6 |
| Dowex | | | | |
| 1% | 47k | 98 | 1.3 | 14.6 |
| 2% | 47k | 99 | 0.8 | 14.7 |
| 3% | 49k | 97 | 0.8 | 15.7 |
| 4% | 49k | 99 | 0.8 | 14.1 |
| 5% | 48k | 96 | 1.5 | 12.4 |

Example 36

The influence of particles functionalized with different surface chemistries. The effects of 1) a dicarboxy-cation exchanger (Chelex-100, Bio-Rad), 2) a sulfo cation exchanger (MacroPrep High S, Bio-Rad), a negatively charged alkyl hydrophobic solid phase (MacroPrep tbutyl, Bio-Rad), a positively charged particle with a lesser concentration of negatively charged groups on the methacrylate polymer backbone (MacroPrep HighQ), and combinations of TREN (BioWorks TREN high) with Dowex AG1x2, were evaluated on an IgG-containing cell culture harvest also containing 241,241 ppm host proteins and 23.3% aggregates. Allantoin was added to a concentration of 1%, then caprylic acid at 0.4%. pH was titrated to 5.2 and the sample mixed for 2 hours until addition of the particles for an additional 4 hours. Data are presented in the table below. Pspecies refers to the various solid phase chemistries.

| Pspecies | Host proteins (ppm) | IgG recovery (%) | Aggregate (%) | FLC (%) |
|---|---|---|---|---|
| CCH | 241k | 100 | 23.3 | 20.9 |
| Chelex | | | | |
| 1% | 33k | 92 | 3.3 | 10.3 |
| 2% | 29k | 92 | 4.0 | 9.3 |
| 4% | 69k | 97 | 19.6 | 12.9 |
| High S | | | | |
| 1% | 94k | 81 | 4.3 | 14.4 |
| 2% | 90k | 74 | 4.8 | 15.2 |
| 4% | 86k | 60 | 2.2 | 18.2 |
| tbutyl | | | | |
| 1% | 86K | 87 | 1.5 | 12.1 |
| 2% | 25K | 86 | 1.9 | 14.4 |
| 4% | 29K | 83 | 2.5 | 15.1 |
| High Q | | | | |
| 1% | 22k | 93 | 2.2 | 9.2 |
| 2% | 18k | 93 | 2.1 | 9.8 |
| 4% | 23k | 93 | 3.1 | 10.7 |
| 1% T/1% D | 9731 | 91 | 1.6 | 7.2 |
| 1% T/2% D | 18k | 90 | 2.0 | 7.5 |
| 2% T/1% D | 17k | 93 | 2.8 | 9.2 |
| 2% T/2% D | 11k | 91 | 1.6 | 6.8 |

Example 37

The influence of solid and dissolved calcium compounds on the disclosed method. An IgG-containing cell culture harvest also containing 652,450 ppm and 34.1% aggregates was treated with 1% allantoin, 0.4% caprylic acid, various concentration of calcium chloride or hydroxyapatite, titrated to pH 5.2 and mixed for two hours. Solids were removed and the samples evaluated. Calcium concentrations ranging from 0.5 to 8.0 mM had no significant effect on IgG recovery. HCP was in the range of ~70,000-80,000 ppm, light chain content was barely reduced, and aggregate levels were generally reduced to ~2.5%. Hydroxyapatite at v:v concentrations of 0.5 to 4% reduced IgG recovery from 79% at 0.5% HA to 38% at 8% HA. Host protein was reduced but the reductions were less than the loss of IgG. Light chain content was not reduced effectively. Aggregates were reduced to the lowest values in the study, but not sufficiently to compensate for antibody losses. Data are presented in the following table. CAspecies refers calcium chloride (CC) or hydroxyapatite (HA) respectively. The line labeled "Base" indicates results obtained without any calcium additives.

| CAspecies | Host proteins (ppm) | IgG recovery (%) | Aggregate (%) | FLC (%) |
|---|---|---|---|---|
| CCH | 652k | 100 | 34.1 | 26.3 |
| Base | 73k | 86 | 2.4 | 23.2 |
| CA | | | | |
| 0.5 mM | 75k | 87 | 4.1 | 24.3 |
| 1 mM | 73k | 86 | 2.6 | 27.8 |
| 2 mM | 71k | 87 | 2.3 | 28.3 |
| 4 mM | 82k | 83 | 2.2 | 25.5 |
| 8 mM | 70k | 83 | 2.6 | 25.1 |
| HA | | | | |
| 0.5% | 58k | 80 | 1.5 | 30.6 |
| 1% | 23k | 75 | 0.8 | 23.8 |
| 2% | 9k | 67 | 1.4 | 24.6 |
| 4% | not detected | 55 | 1.8 | 34.9 |
| 8% | not detected | 38 | 0.2 | 26.8 |

Example 38

Purification and IgM monoclonal antibody. Cell-free cell culture harvest was treated by addition of 1% allantoin, 0.4% caprylic acid, producing an operating pH of about 5.6. The mixture was incubated for 2 hours at room temperature, then TREN particles (Bio-Works TREN high) were added in an amount of 5% v/v, and incubated mixing for 4 hours at room temperature, whereupon solids were removed by centrifugation and microfiltration. Analytical size exclusion chromatography showed that aggregates were reduced from an original concentration of about 23% to less than 0.5%. No host protein peaks were observed, indicating a purity of greater than 98%, not including low molecular weight cell culture media components. In a parallel experiment where the treated IgM was passed through the same depth filter as the IgG in Example 14, the IgM was lost, indicating that it bound to the internal surfaces of the depth filter.

Example 39

The effect of nonionic surfactants. 1% allantoin was added to each of 4 50 mL aliquots of cell culture harvest clarified by centrifugation and microfiltration. One was retained as a control. Tween-20 was added to the other three in amounts of 0.005, 0.01, and 0.02% respectively. The samples were incubated for 10 minutes followed by addition of caprylic acid to 0.4%, and adjustment to pH 5.3 by addition of 1 M acetic acid, then incubation for 2 hours. Samples were removed and filtered for analysis. TREN particles were added to the remainder of the sample in an amount of 5%, mixed for 4 hours, then the solids removed by microfiltration. Up to the point of adding TREN particles, aggregate content was reduced from the control to 0.005% Tween, then again at 0.01% Tween, but did not improve further with 0.02% Tween. Antibody recovery and content of excess free light chain were roughly unchanged. After TREN particle addition, aggregate level was the same across all samples, and light chain content was little-affected, but IgG recovery increased with Tween content up to 0.01% though not further at 0.02%.

| OM | Host proteins (ppm) | IgG recovery (%) | Aggregate (%) | FLC (%) |
|---|---|---|---|---|
| CCH Before TREN Tween-20 | 416k | 100 | 20.3 | 33.4 |
| 0.000% | 137k | 91 | 20.8 | 26.7 |
| 0.005% | 132k | 89 | 16.8 | 25.2 |
| 0.01% | 160k | 90 | 5.9 | 25.7 |
| 0.02% | 151k | 89 | 7.5 | 26.6 |
| After TREN Tween-20 | | | | |
| 0.000% | 6109 | 78 | 1.7 | 0.4 |
| 0.005% | 5627 | 81 | 1.7 | 0.1 |
| 0.01% | 6247 | 88 | 1.7 | 0.4 |
| 0.02% | 8039 | 87 | 1.8 | 2.1 |

Example 40

The effects of nonionic, zwitterionic, and cationic surfactants. 1% allantoin was added to each of 50 mL aliquots of cell culture harvest clarified by centrifugation and microfiltration. One was retained as a control. The following surfactants were added to each of two aliquots at 0.01% and 0.05% respectively: Glycholic acid ethoxylate 4-nonylphenol ether (Glych., nonionic), Ethylenediamine propoxylate-block-ethoxylate tetrol (TET, nonionic), Brij 58 (Pluronic F-127, nonionic), Triton X-100 (nonionic), Nonidet P40 (nonionic), 3-[(3-cholamidopropyl)dimethylammonio]-1-propanesulfonate hydrate (CHAPS, zwitterionic), Hexadecyltrimethylammonium bromid (CTAB, cationic), Dodecyltrimethylammonium bromide (DDTAB, cationic), decyltrimethylammonium bromide (DTAB) cationic), myristyltrimethylammonium bromide (MTAB, cationic), octadecyltrimethylammonium bromide (OTAB, cationic). The samples were incubated for 10 minutes followed by addition of caprylic acid to 0.4%, and adjustment to pH 5.3 by addition of 1 M acetic acid, then incubation for 2 hours.

| OM | Host proteins (ppm) | IgG recovery (%) | Aggregate (%) | FLC (%) |
|---|---|---|---|---|
| CCH | 394k | 100 | 13.3 | 26.2 |
| CaprAll. | 3928 | 86 | 1.7 | 1.5 |
| Glych.01% | 4209 | 81 | 1.4 | 1.8 |
| Glych.05% | 5655 | 83 | 2.1 | 5.1 |
| F127.01% | 55k | 84 | 1.5 | 1.8 |
| F127.05% | 76k | 85 | 1.8 | 0.5 |
| TET.01% | 5204 | 87 | 1.7 | 6.6 |
| TET.05% | 3138 | 88 | 1.3 | 2.0 |
| Brij.01% | 11k | 87 | 3.5 | 6.5 |
| Brij.05% | 26k | 93 | 1.9 | 1.6 |
| Triton.01% | 7241 | 90 | 1.9 | 1.6 |
| Triton.05% | 16k | 92 | 3.9 | 11.5 |
| Ndet.01% | 7519 | 91 | 1.6 | 1.2 |
| Ndet.05% | 16k | 92 | 3.8 | 10.5 |
| CHAPS.01% | 6884 | 85 | 1.2 | 1.9 |
| CHAPS.05% | 8700 | 89 | 1.8 | 3.3 |
| CTAB.01% | 2278 | 86 | 1.1 | 1.3 |
| CTAB.05% | 23k | 86 | 10.3 | 1.7 |
| DDTAB.01% | 5274 | 90 | 1.2 | 2.0 |
| DDTAB.05% | 76k | 91 | 1.8 | 4.4 |
| DTAB.01% | 7281 | 88 | 1.5 | 23.7 |
| DTAB.05% | 42k | 91 | 1.8 | 13.6 |
| MTAB.01% | 9405 | 89 | 1.3 | 4.9 |
| MTAB.05% | 98k | 90 | 1.7 | 16.9 |
| OTAB.01% | 6155 | 89 | 1.1 | 7.0 |
| OTAB.05% | 53k | 89 | 1.4 | 15.4 |

Example 41

The effects of different fatty acids. 1% allantoin was added to each of 50 mL aliquots of cell culture harvest clarified by centrifugation and microfiltration. One was retained as a control. Caprylic acid to 0.4% was added as another control, and pH adjusted to 5.3 by addition of 1 M acetic acid, then incubated mixing for 2 hours. 5 Aliquots of harvest were treated with 0.1%, 0.2%, 0.3%, 0.4%, and 0.5% 2-ethylhexanoic acid (EHA). These experiments were repeated with 3-heptenoic acid (3HA), then with 3-octenoic acid (3OA), and 8-nonenoic acid (8NA).

| Samp. | Host proteins (ppm) | IgG recovery (%) | Aggregate (%) | FLC (%) |
|---|---|---|---|---|
| CCH | 400k | 100 | 13.8 | 31.4 |
| Capry.4% | 14k | 92 | 1.4 | 5.5 |
| EHA.1% | 226k | 89 | 2.0 | 20.8 |
| EHA.2% | 180k | 92 | 2.0 | 20.7 |
| EHA.3% | 154k | 98 | 1.7 | 20.4 |
| EHA.4% | 214k | 89 | 1.7 | 20.9 |
| EHA.5% | 188k | 87 | 1.7 | 20.2 |
| 3HA.1% | 123k | 79 | 1.9 | 22.1 |
| 3HA.2% | 130k | 78 | 1.7 | 21.3 |
| 3HA.3% | 135k | 79 | 1.6 | 21.1 |

-continued

| Samp. | Host proteins (ppm) | IgG recovery (%) | Aggregate (%) | FLC (%) |
|---|---|---|---|---|
| 3HA.4% | 113k | 76 | 1.5 | 20.2 |
| 3HA.5% | 116k | 75 | 1.6 | 20.2 |
| 3OA.1% | 123k | 79 | 1.9 | 21.9 |
| 3OA.2% | 108k | 78 | 1.6 | 21.6 |
| 3OA.3% | 107k | 78 | 1.6 | 19.7 |
| 3OA.4% | 84k | 74 | 1.3 | 13.3 |
| 3OA.5% | 23k | 69 | 1.3 | 6.7 |
| 8NA.1% | 160k | 70 | 2.0 | 26.9 |
| 8NA.2% | 160k | 85 | — | 25.7 |
| 8NA.3% | 123 | 83 | 1.7 | 19.3 |
| 8NA.4% | 9735 | 85 | 1.5 | 4.9 |
| 8NA.5% | 1600 | 83 | 1.4 | 2.6 |

Example 42

Comparison of octanoic acid and 8-heptenoic acid, with and without functionalized particles. 1% allantoin was added to each of 50 mL aliquots of cell culture harvest clarified by centrifugation and microfiltration. One was retained as a control. Caprylic acid to 0.4% was added as another control, and pH adjusted to 5.3 by addition of 1 M acetic acid. The mixture incubated mixing for 2 hours and a sample was removed for testing, then TREN particles were added in an amount of 5% (v:v), and incubated mixing for an additional 4 hours. Solids were removed by microfiltration then analysed. This experimental format was repeated with 8-heptenoic acid at 0.4%, 0.5%, and 0.6%.

| Samp. | Host proteins (ppm) | IgG recovery (%) | Aggregate (%) | FLC (%) |
|---|---|---|---|---|
| CCH Before TREN | 416k | 100 | 20.3 | 33.4 |
| Capry.4% | 137k | 91 | 20.8 | 26.7 |
| 8NA.4% | 147k | 91 | 18.6 | 26.6 |
| 8NA.5% | 124k | 90 | — | 22.1 |
| 8NA.6% After TREN | 71k | 89 | 14.0 | 21.8 |
| Capry.4% | 6108 | 78 | 17 | 0.4 |
| 8NA.4% | 4353 | 91 | 1.8 | 1.7 |
| 8NA.5% | 4561 | 78 | 1.5 | nd |
| 8NA.6% | 6225 | 59 | 0.9 | nd |

As illustrated by the examples, the disclosed methods may be combined with other purification methods to achieve higher levels of purification. Examples of such other purification methods include but are not limited to other methods commonly used for purification of IgG, such as protein A and other forms of affinity chromatography, anion exchange chromatography, cation exchange chromatography, hydrophobic interaction chromatography, and mixed mode chromatography methods; also methods of precipitation, including antibody precipitation with nonionic polymers such as polyethylene glycol or antibody precipitation with salts such as ammonium sulfate, sodium sulfate, potassium phosphate, sodium citrate, or potassium citrate; also methods of crystallization and two-phase aqueous extraction. It is within the purview of a person of ordinary skill in the art to develop appropriate conditions for the various methods and integrate them with the methods disclosed herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and, attached claims are approximations that may vary depending upon the desired performance sought to be obtained by the present invention.

Many modifications and variations of the invention can be made without departing from their spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of purifying an antibody comprising:
   (a) contacting a cell culture harvest or a protein preparation comprising at least one antibody with at least one fatty acid to form a mixture, wherein the at least one fatty acid is selected from enanthic (heptanoic) acid, caprylic (octanoic) acid, octenoic acid, pelargonic (nonanoic) acid, nonenoic acid, and capric (decanoic) acid;
   (b) contacting the mixture with (i) one or more solid substrates comprising a metal binding functional group selected from the group consisting of tris(2-aminoethyl)amine, diethylenetriamine, triethylenetriamine, tetraethylenepentamine, polypropylenimine tetramine, poly(amidoamine) (PAMAM) dendrimer, and deferoxamine (desferioxamine) and (ii) allantoin, wherein allantoin is present at a concentration in a range from about 0.6 to about 30% (w/v); and
   (c) separating solid materials from the mixture to provide a solution comprising the antibody.

2. The method of claim 1, wherein a total amount of the one or more functionalized substrates is a volumetric proportion of the total volume of the preparation of from about 0.01% to about 20%.

3. The method of claim 1, wherein the at least one fatty acid and the one or more solid substrates are disposed in a single vessel or in a device, wherein the device optionally permits the passage of fluid while preventing the passage of solid materials therethrough.

4. The method of claim 3, wherein the device comprises a porous material selected from the group consisting of a membrane, a monolith, a woven material, a crystalline material, a gelatinous material, a column of packed particles, and combinations thereof.

5. The method of claim 1, wherein solid materials are removed by sedimentation, by sedimentation following centrifugation, by membrane filtration or by depth filtration.

6. The method of claim 5, wherein the membrane filtration or depth filtration comprises a contact surface that is functionalized.

7. The method of claim 1, wherein the cell culture harvest or protein preparation contains cells, and optionally resides in a bioreactor within which the cell culture harvest was generated.

8. The method of claim 1, wherein the at least one fatty acid comprises caprylic (octanoic) acid.

9. The method of claim 1, wherein the at least one fatty acid is present at a concentration in a range selected from the group consisting of: (a) from about 0.05 to about 5%, (b) from about 0.1 to about 1.0%, (c) from about 0.2 to about 0.4%, and (d) from about 0.1 to 0.2%.

10. The method of claim 1, wherein the mixture comprises a surfactant, wherein the surfactant is nonionic, zwitterionic, or cationic.

11. The method of claim 10, wherein the cationic surfactant comprises cetyltrimethylammonium bromide at a concentration ranging from about 0.001% to 0.05%, or from about 0.005% to 0.025%, from about 0.0075% to about 0.01%.

12. The method of claim 1, wherein the one or more solid substrates comprise tris(2-aminoethyl)amine.

13. A method for purifying an antibody comprising:
(a) contacting a cell culture harvest or protein preparation with (i) at least one fatty acid having 8 to 10 carbon atoms, (ii) allantoin, at a concentration of up to about 30%, thereby forming a mixture, and (iii) at least one chemically functionalized solid or soluble substrate, wherein the at least one chemically functionalized solid comprises tris(2-aminoethyl)amine; and
(b) separating solid materials after the contacting to provide a solution comprising the antibody in a soluble form.

* * * * *